United States Patent
Ortiz et al.

(10) Patent No.: US 11,097,130 B2
(45) Date of Patent: Aug. 24, 2021

(54) TARGETING CANCER CELLS SELECTIVELY VIA RESONANT HARMONIC EXCITATION

(71) Applicant: California Institute of Technology, Pasadena, CA (US)

(72) Inventors: Michael Ortiz, Pasadena, CA (US); Stefanie Heyden, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 1029 days.

(21) Appl. No.: 15/373,916

(22) Filed: Dec. 9, 2016

(65) Prior Publication Data

US 2017/0165506 A1 Jun. 15, 2017

Related U.S. Application Data

(60) Provisional application No. 62/265,761, filed on Dec. 10, 2015.

(51) Int. Cl.
*A61N 7/00* (2006.01)

(52) U.S. Cl.
CPC ........ *A61N 7/00* (2013.01); *A61N 2007/0004* (2013.01)

(58) Field of Classification Search
CPC .................. A61N 2007/0004; A61N 7/00
See application file for complete search history.

(56) References Cited

U.S. PATENT DOCUMENTS

| | | | |
|---|---|---|---|
| 8,591,419 B2 | 11/2013 | Tyler | |
| 2005/0214268 A1 | 9/2005 | Cavanagh, III et al. | |
| 2006/0034943 A1* | 2/2006 | Tuszynski | A61K 41/0004 424/649 |
| 2006/0058592 A1* | 3/2006 | Bouma | A61B 5/0059 600/301 |
| 2008/0082110 A1 | 4/2008 | Rodriguez Ponce | |
| 2009/0198231 A1* | 8/2009 | Esser | A61N 1/327 606/41 |
| 2010/0113983 A1 | 5/2010 | Heckerman et al. | |
| 2011/0098987 A1* | 4/2011 | Isoshima | G06F 17/5018 703/1 |
| 2012/0059865 A1* | 3/2012 | Shao | G06F 17/13 708/270 |

(Continued)

OTHER PUBLICATIONS

Fraldi et al., "A frequency-based hypothesis for mechanically targeting and selectively attaching cancer cells". J. R. Soc. Interface 12(111): 20150656, pp. 1-16. Published Oct. 6, 2015. (Year: 2015).*

(Continued)

*Primary Examiner* — Yi-Shan Yang
(74) *Attorney, Agent, or Firm* — KPPB LLP

(57) ABSTRACT

Systems and methods for targeting specific cell types by selective application of ultrasonic harmonic excitation at their resonance frequency ("oncotripsy") are presented. The systems and methods result in the lysis of targeted cell types by using ultrasonic harmonic excitations that have been specifically tuned to disrupt the nuclear membrane of the targeted cells types by inducing a destructive vibrational response therein while leaving non-targeted cell types intact. The target cells types may be cancerous cells.

26 Claims, 21 Drawing Sheets

(56) References Cited

U.S. PATENT DOCUMENTS

| | | | |
|---|---|---|---|
| 2013/0131557 A1* | 5/2013 | Kline | A61N 7/00 601/2 |
| 2017/0266438 A1* | 9/2017 | Sano | A61B 18/1477 |
| 2018/0256922 A1 | 9/2018 | Mittelstein et al. | |

OTHER PUBLICATIONS

Bertoldi et al., "Bloch wave approach for the analysis of sequential bifurcations in bilayer structures", Proc. R. Soc. A 471: 20150493 , published Nov. 6, 2015. (Year: 2015).*
Milner et al., "Finite-element modeling of viscoelastic cells during high-frequency cyclic strain". J. Funct. Biomater 2012, 3, 209-224. (Year: 2012).*
Levental et al., "Matrix crosslinking forces tumor progression by enhancing intergrin signaling", Cell 139, 891-906, 2009. (Year: 2009).*
Kattan , "MatLab guide to finite element", Springer-Verlag Berlin Heidelberg 2008, Chapter 11 and Chapter 15. (Year: 2008).*
Or et al., "Modeling linear vibration of cell nucleus in low intensity ultrasound field"., Ultrasound in Med. & Biol., vol. 35, No. 6, pp. 1015-1025, 2009. (Year: 2009).*
"The cell nucleus". Davidson et al., Molecular Expressions: Cell biology and microscopy, Structure and Function of cells an viruses., 2007 https://micro.magnet.fsu.edu/cells/nucleus/nucleus.html (Year: 2007).*
Bloch, F., Zeitschrift fuur Physik 52, Aug. 10, 1928, p. 555-600.
Caille, N. et al., J. Biomech., vol. 35, 2002, p. 177-178.
Cartagena, A. et al., Biophysical Journal, vol. 106, Mar. 2014, p. 1033-1043.
Clegg, J. S., Am. J. Physiol. 246, 1984, pp. R133-R151.
Cross, S. E. et al., Nature Nanotechnology, Dec. 2, 2007, vol. 2, pp. 780-783.
Dahl, K. N. et al., Journal of Cell Science, Jun. 14, 2004, vol. 117, pp. 4779-4786.
Evans, E. A. et al., Biophys J., vol. 16 (1), 1976, p. 1-11.
Evans, E. A. et al., Biophysical Journal, 1976, vol. 16, p. 585-595.
Fuhrmann, A. et al., Physical Biology, Feb. 7, 2011, vol. 8, p. 1-10.
Guilak, F., Biochemical and Biophysical Research Communications, Dec. 21, 1999, vol. 269, p. 781-786.
Guttman, P. H. et al., American Journal of Cancer, 1935, p. 802-806.
Handwerger, K. E. et al., Mol Biol Cell, Jan. 2005, vol. 16. No. 1, pp. 202-211.
Houchmandzadeh, B. et al., J. Cell Biol., Oct. 6, 1997, vol. 139, p. 1-12.
Jay, A. W. L., Biophys J., 1973, vol. 13 (11), pp. 1166-1182.
Kim, Y. et al., Med. Biol. Engineering and Computing, Jan. 8, 2011, vol. 49 (4), pp. 453-462.
Kochmann, D. M. et al., Proc. R. Soc. A, Feb. 15, 2012, p. 1-25.
Konno, K. et al., IFMBE Proceedings, vol. 39, 2013, Springer, p. 290-293.
Krodel, S. et al I., "3D Auxetic Microlattices with Independently Controllable Acoustic Band Gaps and Quasi-Static Elastic Moduli", Advanced Engineering Materials, 2014, vol. 16 (4), pp. 357-363.
Lammertink, B. H. A. et al., Frontiers in Pharmacology, Jul. 10, 2015, vol. 6 (138), pp. 1-17.
Lentacker, I. et al., Advanced Drug Delivery Reviews, Nov. 21, 2013, vol. 72, pp. 49-64.
Levental, K. R. et al., Cell, Nov. 25, 2009, vol. 139, pp. 891-906.
Li, F. et al., Biophysical Journal, Aug. 2013, vol. 105, pp. 872-879.
Lieleg, O. et al., Biophysical Journal, Jun. 2009, vol. 96, pp. 4725-4732.
Lodish, H. et al., Molecular Cell Biology, 5th Edition, 2004, WH Freeman, New York. (presented in 5 parts).
Moran, U. et al., Cell 141, Jun. 25, 2010, p. 1-2.
Paszek, M. J. et al., Cancer Cell, Sep. 2005, vol. 8, pp. 241-254.
Richard, Jean-Damien et al., "Ventilator-Induced Lung Injury", Organ System Function and Failure, Part II, 1st Edition, 2006, CRC Press, Boca Raton, FL, Chapter 45, pp. 719-730.
Schrader, J. et al., Hepatology, vol. 53 (4), 2011, p. 1192-1205.
Swaminathan et al., Cancer Research, Jun. 3, 2011, vol. 71 (15), p. 5075-5080.
Zhang, G. et al., World Journal of Gastroenterology, Apr. 15, 2002, vol. 8 (2), pp. 243-246.
Aubry et al., "The road to clinical use of high-intensity focused ultrasound for liver cancer: technical and clinical consensus", Journal of Therapeutic Ultrasound, Aug. 1, 2013, vol. 1, No. 13, 7 pages, https://doi.org/10.1186/2050-5736-1-13.
Cohen-Inbar et al., "Focused ultrasound-aided immunomodulation in glioblastoma multiforme: a therapeutic concept", Journal of Therapeutic Ultrasound, Jan. 22, 2016, vol. 4, No. 2, 9 pages, https://doi.org/10.1186/s40349-016-0046-y.
Couture et al., "Review of ultrasound mediated drug delivery for cancer treatment: updates from pre-clinical studies", Translational Cancer Research, vol. 3, No. 5, Oct. 2014, pp. 494-511.
Eisenmenger, "The mechanisms of stone fragmentation in ESWL", Ultrasound in Medicine & Biology, vol. 27, Issue 5, May 2001, pp. 683-693, https://doi.org/10.1016/S0301-5629(01)00345-3.
Fan et al., "Spatiotemporally controlled single cell sonoporation", PNAS, Oct. 9, 2012, vol. 109, No. 41, pp. 16486-16491, https://doi.org/10.1073/pnas.1208198109.
Feril Jr. et al., "Therapeutic potential of low-intensity ultrasound (part 1): thermal and sonomechanical effects", Journal of Medical Ultrasonics, Dec. 2008, vol. 35, Issue 4, pp. 153-160.
Hersh et al., "Emerging Applications of Therapeutic Ultrasound in Neuro-Oncology: Moving Beyond Tumor Ablation", Neurosurgery, vol. 79, Issue 5, Nov. 1, 2016, pp. 643-654, https://doi.org/10.1227/NEU.0000000000001399.
Heyden et al., "Oncotripsy: Targeting cancer cells selectively via resonant harmonic excitation", Journal of the Mechanics and Physics of Solids, vol. 92, Jul. 2016, pp. 164-175, https://doi.org/10.1016/j.jmps.2016.04.016.
Hsiao et al., "Clinical Application of High-intensity Focused Ultrasound in Cancer Therapy", Journal of Cancer, Jan. 3, 2016, vol. 7, No. 3, pp. 225-231, doi: 10.7150/jca.13906.
Kondziolka et al., "The biology of radiosurgery and its clinical applications for brain tumors", Neuro-Oncology, vol. 17, Issue 1, Jan. 1, 2015, pp. 29-44, https://doi.org/10.1093/neuonc/nou284.
Krasovitski et al., "Intramembrane cavitation as a unifying mechanism for ultrasound-induced bioeffects", PNAS, Feb. 7, 2011, 6 pages, https://doi.org/10.1073/pnas.1015771108.
Lekka, "Discrimination Between Normal and Cancerous Cells Using AFM", BioNanoScience, Mar. 2016, vol. 6, Issue 1, pp. 65-80, DOI 10.1007/s12668-016-0191-3.
Louw et al., "Mechanotransduction of Ultrasound is Frequency Dependent Below the Cavitation Threshold", Ultrasound in Medicine & Biology, vol. 39, Issue 7, Jul. 2013, pp. 1303-1319, https://doi.org/10.1016/j.ultrasmedbio.2013.01.015.
Malietzis et al., "High-intensity focused ultrasound: advances in technology and experimental trials support enhanced utility of focused ultrasound surgery in oncology", The British Journal of Radiology, vol. 86, Issue 1024, 2013, 12 pages, https://doi.org/10.1259/bjr.20130044.
McGahan et al., "Hepatic Ablation with Use of Radio-Frequency Electrocautery in the Animal Model", Journal of Vascular and Interventional Radiology, May 1992, vol. 3, Issue 2, pp. 291-297, DOI: https://doi.org/10.1016/S1051-0443(92)72028-4.
Niranjan et al., "Role of adjuvant or salvage radiosurgery in the management of unresected residual or progressive glioblastoma multiforme in the pre-bevacizumab era", Journal of Neurosurgery, Apr. 2015, vol. 122, No. 4, pp. 757-765.
Pogoda et al., "Compression stiffening of brain and its effect on mechanosensing by glioma cells", New Journal of Physics, vol. 16, Jul. 2014, Article 075002, 16 pages.
Rooze et al., "Dissolved gas and ultrasonic cavitation—A review", Ultrasonics Sonochemistry, vol. 20, Issue 1, Jan. 2013, pp. 1-11, https://doi.org/10.1016/j.ultsonch.2012.04.013.
Samandari et al., "Ultrasound induced strain cytoskeleton rearrangement: An experimental and simulation study", Journal of Biomechanics, vol. 60, Jul. 26, 2017, pp. 39-47, https://doi.org/10.1016/j.jbiomech.2017.06.003.

(56) References Cited

OTHER PUBLICATIONS

Silvestrini et al., "Priming is key to effective incorporation of image-guided thermal ablation into immunotherapy protocols", JCI Insight, Mar. 23, 2017, vol. 2, No. 6, Article e90521, 16 pages, doi: 10.1172/jci.insight.90521.

Teicher, "Perspective: Opportunities in recalcitrant, rare and neglected tumors", Oncology Reports, Sep. 2013, vol. 30, Issue 3, pp. 1030-1034, Published online on Jul. 2, 2013, https://doi.org/10.3892/or.2013.2581.

Ter Haar et al., "Tissue Destruction with Focused Ultrasound in vivo", European Urology, 1993, vol. 23, Suppl. 1, pp. 8-11, https://doi.org/10.1159/000474672.

Unga et al., "Ultrasound induced cancer immunotherapy", Advanced Drug Delivery Reviews, vol. 72, Jun. 15, 2014, pp. 144-153, https://doi.org/10.1016/j.addr.2014.03.004.

Venkatesh et al., "MR Elastography of Liver Tumors: Preliminary Results", American Journal of Roentgenology, Jun. 2008, vol. 190, No. 6, pp. 1534-1540.

Zhang et al., "Effects of High-Intensity Focused Ultrasound for Treatment of Abdominal Lymph Node Metastasis From Gastric Cancer", Journal of Ultrasound in Medicine, vol. 34, Issue 3, Mar. 2015, pp. 435-440, https://doi.org/10.7863/ultra.34.3.435.

Zhou, "High intensity focused ultrasound in clinical tumor ablation", World Journal of Clinical Oncology, Jan. 10, 2011, vol. 2, No. 1, pp. 8-27, doi: 10.5306/wjco.v2.i1.8.

\* cited by examiner

US 11,097,130 B2

TARGETING CANCER CELLS SELECTIVELY VIA RESONANT HARMONIC EXCITATION

STATEMENT OF RELATED APPLICATIONS

The current application claims priority to U.S. Provisional Application No. 62/265,761, filed Dec. 10, 2015, the disclosure of which is incorporated herein by reference.

FIELD OF THE INVENTION

The current description is directed to systems and methods for performing targeted cell lysis by resonant harmonic excitation.

BACKGROUND OF THE INVENTION

Harmonic excitation refers to a sinusoidal external force of a certain frequency applied to a system. One response of a system to harmonic excitation is resonance. Resonance occurs when the external excitation applied has the same frequency as the natural frequency of the system. It leads to large displacements and can cause a system to exceed its elastic range and fail structurally. One example of such a resonance occurs when a glass is broken via the application of an auditory harmonic excitation. Harmonic excitation also can occur in many other contexts.

SUMMARY OF THE INVENTION

In accordance with many embodiments, the disclosure is directed to systems and methods for targeting specific cell types by selective application of ultrasonic harmonic excitation at their resonance frequency.

Various embodiments are directed to methods of performing oncotripsy including:
 identifying a target cell type in an organism and identifying at least one healthy cell type present in the organism in the vicinity of the target cell type;
 selecting a target cell eigenfrequency for the target cell type such that a spectral gap exists between the target cell eigenfrequency and all possible eigenfrequencies of the at least one healthy cell type;
 subjecting at least one area of the organism containing target cells to a harmonic excitation tuned to the target cell eigenfrequency for a duration sufficient to induce a transient destructive resonance within a target cell resonant mode; and
 wherein the spectral gap is sufficiently large such that the transient destructive resonance is induced within the target cells prior to a transient destructive resonance being induced within the a healthy cell resonant mode of the at least one healthy cell type.

In various other embodiments the harmonic excitation is an ultrasonic harmonic excitation.

In still various other embodiments the destructive resonance disrupts the nuclear membrane of the target cells inducing lysis.

In yet various other embodiments the growth rate of the target cell resonant mode is greater than the growth rate of the healthy cell resonant mode. In some such embodiments, the harmonic excitation has a frequency range of about 80 kHz, a duration of at least 70 µs, and a power density of at least 0.8 W/cm2.

In still yet various other embodiments the eigenfrequencies of the target and healthy cells are determined by modeling the cells wherein the plasma membrane, nuclear envelope, cytoplasm, nucleoplasm, and nucleolus are modeled as a spheroidal shape; wherein the plasma membrane is modeled as a lipid bilayer composed of two regular layers of lipid molecules; wherein the nuclear envelope is modeled as a double lipid bilayer membrane; and mixtures thereof. In some such embodiments, the eigenfrequencies of the target and healthy cells are determined by considering the nucleus-to-cell volume ratios of the cells. In still other such embodiments a nucleus-to-cell volume ratio of greater than one is indicative of a target cell.

In still yet various other embodiments the eigenfrequencies of the target and healthy cells are determined by modelling the elasticity of one or more cell constituents using a Mooney-Rivlin-type strain energy density calculation.

In still yet various other embodiments the eigenfrequencies of the target and healthy cells are determined using a finite element mesh. In some such embodiments the cytoplasm, nucleoplasm and nucleolus of the target and healthy cells are discretized using linear tetrahedral elements, and whereas the plasma membrane and nuclear envelope are discretized using linear triangular membrane elements. In some other such embodiments the cells are approximated as elliptical cells embedded into an extra-cellular matrix modelled using a standard Bloch wave theory.

In still yet various other embodiments the target cell is a cancerous cell. In some such embodiments the target cell eigenfrequency is around 500,000 rad/s.

In still yet various other embodiments the target cell eigenfrequency of the target cell is selected such that the harmonic excitation creates a transient destructive resonance with a modal selectivity configured to induce lysis in a specific cell component of the target cell. In some such embodiments the target cell is cancerous, and the target cell eigenfrequency is selected to induce a transient destructive resonance within the plasma membrane of the target cell.

Many embodiments are directed to methods of determining oncotripsy conditions including:
 identifying a target cell type in an organism and identifying at least one healthy cell type present in the organism in the vicinity of the target cell type;
 determining a target cell eigenfrequency for the target cell type such that a spectral gap exists between the target cell eigenfrequency and all possible eigenfrequencies of the at least one healthy cell type; and
 wherein the spectral gap is sufficiently large such that the transient destructive resonance is induced within the target cells prior to a transient destructive resonance being induced within the a healthy cell resonant mode of the at least one healthy cell type.

In many other embodiments the eigenfrequencies of the target and healthy cells are determined by modeling the cells wherein the plasma membrane, nuclear envelope, cytoplasm, nucleoplasm, and nucleolus are modeled as a spheroidal shape; wherein the plasma membrane is modeled as a lipid bilayer composed of two regular layers of lipid molecules; wherein the nuclear envelope is modeled as a double lipid bilayer membrane; and mixtures thereof. In some such embodiments the eigenfrequencies of the target and healthy cells are determined by considering one or more of the following properties a nucleus-to-cell volume ratios of the cells, the stiffness of an extra-cellular matrix associated with the cells, and the softness of a cellular material of the cells. In other such embodiments a nucleus-to-cell volume ratio of the target cell is greater than a nucleus-to-cell volume ratio of the healthy cells. In still other such embodiments the extra-cellular matrix of the target cell is stiffer than that of the healthy cells. In yet other such embodiments the cellular material of the target cell is softer than that of the healthy cells.

In still many other embodiments the eigenfrequencies of the target and healthy cells are determined by modelling the elasticity of one or more cell constituents using a Mooney-Rivlin-type strain energy density calculation.

In yet many other embodiments the eigenfrequencies of the target and healthy cells are determined using a finite element mesh. In some such embodiments the cytoplasm, nucleoplasm and nucleolus of the target and healthy cells are discretized using linear tetrahedral elements, and whereas the plasma membrane and nuclear envelope are discretized using linear triangular membrane elements. In other such embodiments the cells are approximated as elliptical cells embedded into an extra-cellular matrix modelled using a standard Bloch wave theory.

Additional embodiments are directed to a system for performing oncotripsy including:
a source of harmonic excitation;
a source controller for selecting a harmonic excitation frequency corresponding to a target cell eigenfrequency for a target cell type such that a spectral gap exists between the target cell eigenfrequency and all possible eigenfrequencies of at least one healthy cell type; and
wherein the spectral gap is sufficiently large such that a transient destructive resonance is induced within the target cells prior to a transient destructive resonance being induced within the a healthy cell resonant mode of the at least one healthy cell type.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

These and other features and advantages of the present invention will be better understood by reference to the following detailed description when considered in conjunction with the accompanying data and figures, wherein.

DETAILED DESCRIPTION OF THE INVENTION

Figure 1:
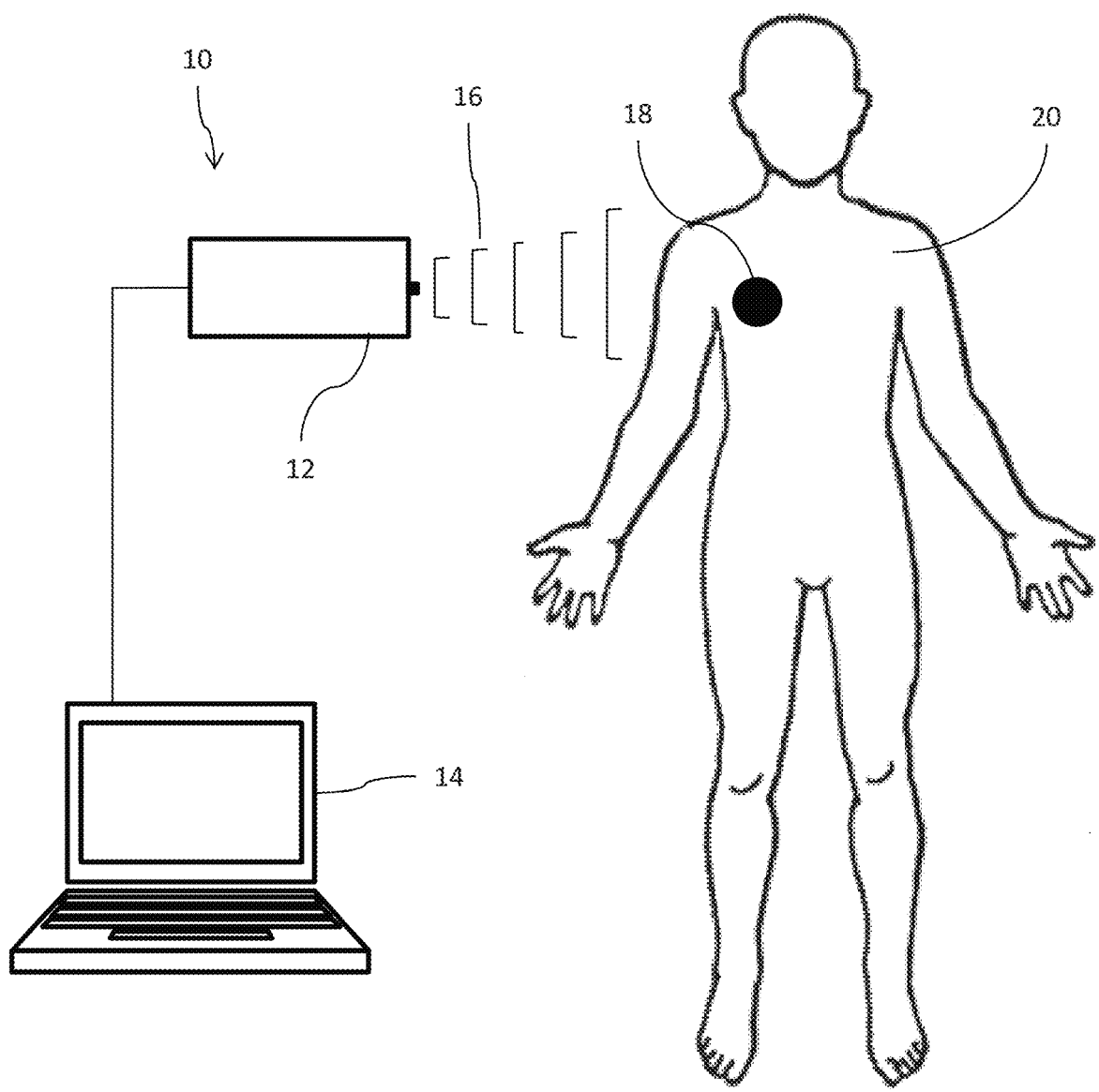
FIG. 1 provides a schematic diagram of a system for application of an ultrasonic harmonic excitation in accordance with embodiments.

Turning to the drawings and detailed description, systems and methods for targeting specific cell types by selective application of ultrasonic harmonic excitation at their resonance frequency are described, such methods and systems maybe be referred to as "oncotripsy" hereinafter. In many embodiments, the systems and methods result in the lysis of targeted cell types by using ultrasonic harmonic excitations that have been specifically tuned to disrupt the nuclear membrane of the targeted cells types by inducing a destructive vibrational response therein while leaving non-targeted cell types intact. In various such embodiments the target cells types are cancerous cells.

Various embodiments are also directed to geometric models, material models, and material parameters that allow for finite-element analyses to determine harmonic excitation conditions capable of creating a lysis-inducing resonance in a targeted cell type. In various embodiments, such embodiments take into account the cytoplasm, nucleus and nucleolus, as well as the plasma membrane and nuclear envelope. Using such embodiments, a spectral gap between the natural frequencies and, resonant growth rates of healthy and cancerous cells may be identified. In many embodiments, material properties identified may be varied within a pathophysiologically-relevant range. In certain embodiments a normal mode analysis in the harmonic range reveals the existence of a healthy-to-cancerous spectral gap in ground frequency of the order of 230,000 rad/s, or 36.6 kHz. Accordingly, many embodiments are directed to methods and systems for provoking a transient response of cells to harmonic excitation within these ranges to induce lysis of cancerous cells without damage to healthy cells. In many such embodiments ultrasound actuation may be readily delivered, e.g., by means of commercial low frequency and low-intensity ultrasonic transducers. In some such embodiments the transducers are tuned to produce ultrasound pulses in the frequency range of 80 kHz, with a duration in the range of 70 μs, and with a power density in the range of 0.8 W/cm$^2$.

Various other embodiments are directed to methods of determining the accuracy of the finite-element model by means of a comparison between numerical and analytical solutions for the eigenmodes of a model spherical cell. The results of the modal analysis are verified by simulating the fully nonlinear transient response of healthy and cancerous cells at resonance. In some such embodiments a fully nonlinear analysis can be used to confirm that cancerous cells can be selectively taken to lysis by the application of carefully tuned ultrasound harmonic excitation while simultaneously leaving healthy cells intact.

Studies of Cellular Morphologies

Aberrations in both cellular morphology and material properties of different cell constituents are indications of various forms of cancerous tissues. For instance, a criterion for malignancy is the size difference between normal nuclei, with an average diameter of 7 to 9 microns, and malignant nuclei, which can reach a diameter of over 50 microns. (Berman, J. J., 2011. Precancer: The Beginning and the End of Cancer, 1st Edition. Jones & Bartlett Publishers, London, United Kingdom, the disclosure of which is incorporated herein by reference.) Early studies have shown that the nuclear-nucleolar volume ratios in normal tissues and benign as well as malignant tumors do not differ quantitatively. Nucleoli volumes of normal tissues, however, are found to be significantly smaller than the volume of nucleoli in cancerous tissues. (See, e.g., Guttman, P. H., Halpern, S., 1935. *Am. J. Cancer,* 25, 802-806, the disclosure of which is incorporated herein by reference.) Similarly, the mechanical stiffness of various cell components has been found to vary significantly in healthy and diseased tissues. The stiffness of live metastatic cancer cells was also investigated using atomic force microscopy, showing that cancer cells are more than 80% softer than healthy cells. (See, e.g., Cross, S. E., et al., 2007. *Nature Nanotechnology* 2, 780-783, the disclosure of which is incorporated herein by reference.) Other cancer types, including lung, breast and pancreas cancer, display similar stiffness characteristics. Furthermore, using a magnetic tweezer, it has been found that cancer cells with the lowest invasion and migratory potential are five times stiffer than cancer cells with the highest potential. (See, e.g., Swaminathan, et al., 2011. *Cancer Research* 71 (15), 5075-5080, the disclosure of which is incorporated herein by reference.) Likewise, increasing stiffness of the extracellular matrix (ECM) was reported to promote hepatocellular carcinoma (HCC) cell proliferation, thus being a strong predictor for HCC development. (See, e.g., Schrader, J., et al., 2011. *Hepatology* 53 (4), 1192-1205, the disclosure of which is incorporated herein by reference.) Moreover, enhanced cell contractility due to increased matrix stiffness results in an enhanced transformation of mammary epithelial cells. (See, e.g., Paszek, M. J., et al., 2005. *Cancer Cell* 8, 241-254, the disclosure of which is incorporated herein by reference.) Conversely, a decrease in tissue stiffness has been found to impede malignant growth in a murine model of breast cancer. (See, e.g., Levental, K. R., Y et al., 2009. *Cell* 139, 891-906, the disclosure of which is incorporated herein by reference.)

Various experimental techniques have been utilized in order to quantitatively assess the material properties of individual cell constituents in both healthy and diseased tissues. The inhomogeneity in stiffness of the living cell nucleus in normal human osteoblasts has been investigated using a noninvasive sensing system. (See, e.g., Konno, K., et al., 2013. *IFMBE Proceedings*. Vol. 39. Springer, pp. 290-293, the disclosure of which is incorporated herein by reference.) In such studies, the stiffness of the nucleolus is found to be relatively higher compared to that of other nuclear domains. Similarly, a difference in mass density between nucleolus and nucleoplasm in the *xenopus* oocyte nucleus has also been determined by recourse to refractive indices. (See, e.g., Handwerger, K. E., et al., 2005. *Mol Biol Cell* 16 (1), 202-211, the disclosure of which is incorporated herein by reference.) The elastic modulus of both isolated chromosomes and entire nuclei in epithelial cells have also been determined. Specifically, it has been shown that mitotic chromosomes behave linear elastically up to 200% extension. (See, e.g., Houchmandzadeh, B., et al., 1997. *J. Cell Biol.* 139, 1-12, the disclosure of which is incorporated herein by reference.) Experiments additionally measured the network elastic modulus of the nuclear envelope, independently of the nucleoplasm, by means of micropipette aspiration, suggesting that the nuclear envelope is much stiffer and stronger than the plasma membranes of cells. (See, e.g., Dahl, K. N., et al., 2004. *Journal of Cell Science* 117, 4779-4786, the disclosure of which is incorporated herein by reference.) In addition, wrinkling phenomena near the entrance of the micropipette were indicative of the solid-like behavior of the envelope. The elastic moduli of both cytoplasm and nucleus of hepatocellular carcinoma cells was also estimated based on force-displacement curves obtained from atomic force microscopy. (See, e.g., Kim, Y., et al., 2011. *Med. Biol. Engineering and Computing* 49 (4), 453-462, the disclosure of which is incorporated herein by reference.) In addition, micropipette aspiration techniques have been used in order to further elucidate the viscoelastic behavior of human hepatocytes and hepatocellular carcinoma cells. Based on these studies, it has been concluded that a change in the viscoelastic properties of cancer cells could affect metastasis and tumor cell invasion. (See, e.g., Zhang, G., et al., 2002. *World Journal of Gastroenterology* 8 (2), 243-246, the disclosure of which is incorporated herein by reference.) The increased compliance of cancerous and pre-cancerous cells was also investigated using atomic force microscopy to determine the mechanical stiffness of normal, metaplastic and dysplastic cells, showing a decrease in Young's modulus from normal to cancerous cells. (See, e.g., Fuhrmann, A., et al., 2011. *Physical Biology* 8, 1-10, the disclosure of which is incorporated herein by reference.)

A large body of literature has been also devoted to the investigation of the effects of carefully tuned ultrasound pulses on sonoporation, i.e., the formation of temporary pores in the cell membrane, and on enhanced endocytosis. (See, e.g., Lentacker, I., et al., 2014. *Advanced Drug Delivery Reviews* 72, 49-64, the disclosure of which is incorporated herein by reference.) Microbubble-assisted ultrasound has been shown to facilitate drug delivery, e.g., for enhancing the transport of chemotherapeutic agents into living cells. (See, e.g., Lammertink, B. H. A., et al., 2015. *Frontiers in Pharmacology* 6 (138), the disclosure of which is incorporated herein by reference.) The underlying biophysical mechanisms leading to an enhanced membrane permeability of cells are shear stresses induced by oscillating microbubbles, in the case of stable cavitation, and shock waves generated during microbubble collapse, in the case of inertial cavitation. (See, Lentacker, cited above).

Embodiments herein recognize that, the distinctive physical properties of different cell types provides a pathway for selectively targeting different cell types, and systems and methods are provided that utilize ultrasound harmonic excitation to induce resonant response of cells to selectively induce lysis in selected cells, such as, for example, cancer cells.

Systems for Performing Oncotripsy

Turning now to the systems for performing oncoptripsy, as shown in FIG. 1, in some exemplary embodiments the system (10) generally comprises a tunable source of ultrasonic emission (12) in signal communication with a control system (14) that allows the frequency of the ultrasonic emission (16) to be tuned over a desired range selected by the user. During operation, the ultrasonic emission source would be placed into a suitable position relative to the cells (18) in a patient (20) to be targeted and the harmonic excitation activated at an excitation frequency configured to selectively create destructive resonance within targeted cells (e.g., cancerous or other diseased cells) for a time period sufficient to result in lysis of the cells.

It will be understood that any suitable ultrasonic emitter and control system capable of selecting an excitation frequency and an emissive time suitable for inducing lysis within a target cell may be utilized in accordance with embodiments. For example, in many embodiments the system incorporates a commercial low frequency and low-intensity ultrasonic transducer and controller. In some such embodiments the transducers are selected such that they are capable of being tuned to produce ultrasound pulses in the frequency range of up to and around 80 kHz, with a duration in the range of at least 70 μs, and with a power density in the range of at least 0.8 W/cm².

Although specific excitation frequencies are described herein, the transient response of cells at resonance may additionally incorporate different types of excitations, which directly corresponds to a change of $F_n(t)$ in (EQ. 26).

Selection of Harmonic Excitation Frequency for Cell Targeting

Although the above description has focused on a system for applying a harmonic excitation to a cellular system including target and non-target cells to perform oncotripsy thereon (e.g., lysing the target cells and leaving the non-target cells unaffected) it should be understood that embodiments are also directed to methods for performing oncotripsy that include determining an excitation range (frequency and duration) that will allow for the selective use of harmonic excitation to induce oncolysis or 'bursting' of target (e.g., cancerous cells), by tuned ultrasound harmonic excitation while simultaneously leaving normal cells intact, i.e., oncotripsy. Accordingly, in various embodiments the vibrational response of target and healthy cells can be used to allow one to choose the frequency of the harmonic excitation to induce lysis of the nucleolus membrane of cancerous cells selectively such that no risk arises to the healthy cells.

Figure 2A:
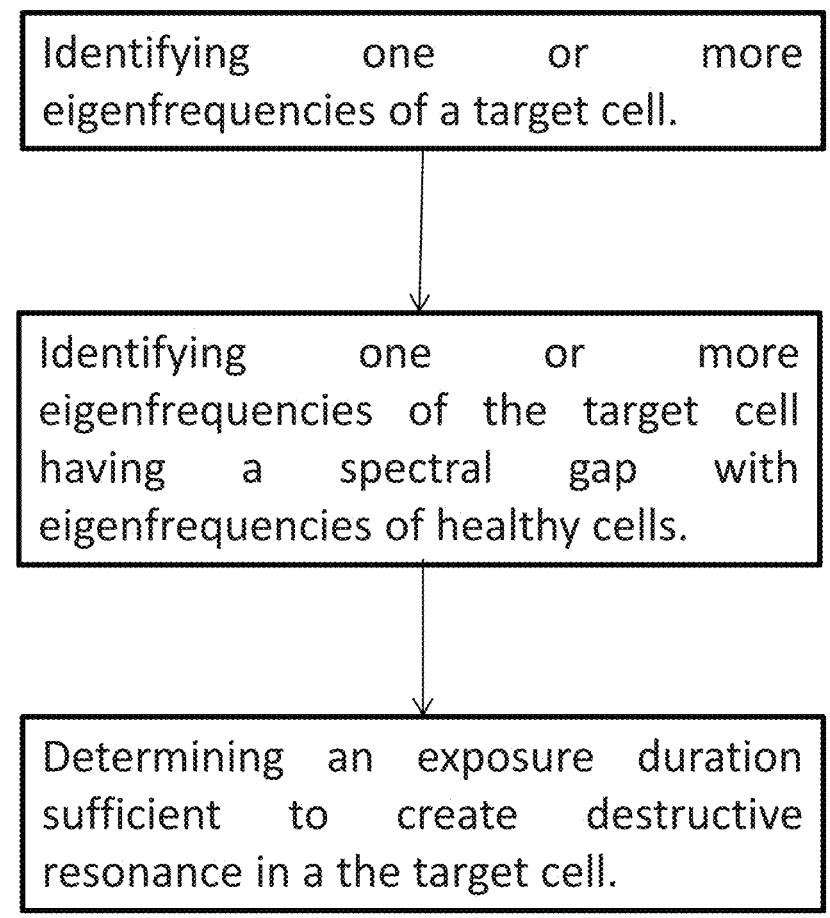
FIG. 2a provides a flowchart of a method for performing oncotripsy, in accordance with embodiments.

Many methods are available for determining appropriate oncotripsy conditions for a specific target cell type. As shown in the flow chart provided in FIG. 2a, in some embodiments the technique includes identifying a destructive excitation frequency (i.e., eigenfrequency) at which destructive resonance will occur within the target cell and healthy cells, identifying the resonant gap between the destructive excitation frequencies of the target and healthy cells, and then determining an exposure at the destructive excitation frequency of the target cell suitable to ensure lysis of the target cells without causing damage to the healthy cells. Each of these steps will be described in greater detail in accordance with embodiments described below.

Figure 2B:
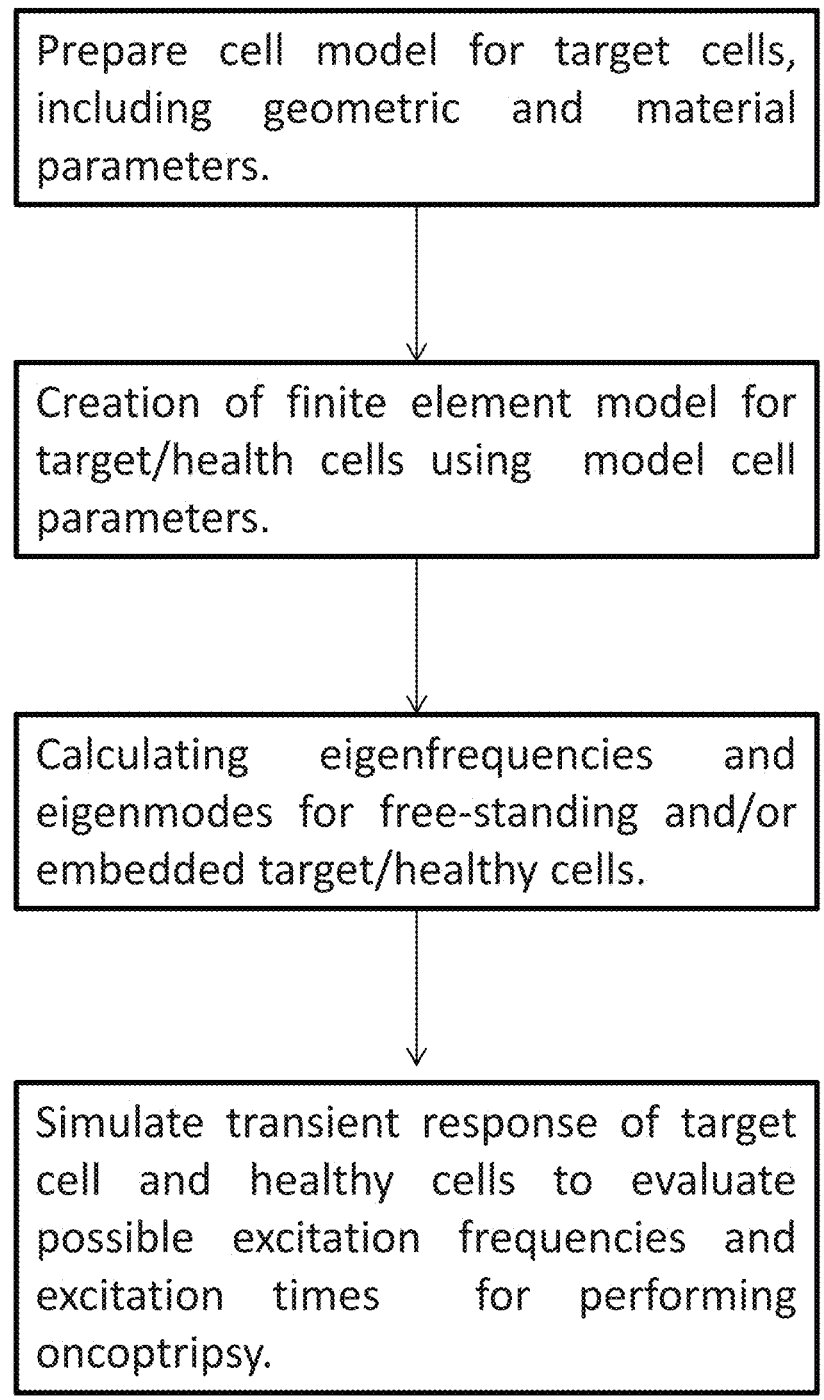
FIG. 2b provides a flowchart of a method for determining resonance frequencies for use in such ultrasonic harmonic excitation systems, in accordance with embodiments.

As shown in FIG. 2b, in various embodiments the dynamical response of healthy and cancerous cells under harmonic excitation is determined using methods in which the destructive excitation frequencies and related resonance gap between the target and healthy cells are first determined by identifying differences in the underlying geometric and material parameters of the cells. In various embodiments these physical parameter are then used to construct a finite element model used for modal analysis, and then calculate the eigenfrequencies and eigenmodes of both free-standing cells (i.e., cells embedded in a representative volume of ECM with harmonic excitation applied to the boundary), and periodic distributions of cells, (i.e., cells embedded in a representative volume of ECM subject to periodic boundary conditions corresponding to Bloch's theorem). Finally, to determine the response of target and healthy cells to the identified harmonic excitation, resonant growth rates that simulate the transient response of both target (e.g., cancerous) and healthy cells excited at resonance in a fully-nonlinear setting are determined by means of implicit dynamics calculations.

Geometry and Material Parameters

Turning to the geometry and material parameters for use in determining the necessary dynamics calculations, various embodiments may utilize a number of different factors in accordance with the following guidelines.

The nucleus, the largest cellular organelle, occupies about 10% of the total cell volume in mammalian cells. (See, e.g., Lodish, H., et al., 2004. *Molecular Cell Biology*, 5th Edition. WH Freeman, New York; and Alberts, B., et al., 2002. Molecular Biology of the Cell, 4th Edition. Garland Science, New York, the disclosures of which are incorporated herein by reference). It contains the nucleolus, which is embedded in the nucleoplasm, a viscous solid similar in composition to the cytosol surrounding the nucleus. (See, e.g., Clegg, J. S., 1984. *Am. J. Physiol.* 246, the disclosure of which is incorporated herein by reference.) In many embodiments of a method for determining the harmonic excitation, the cytosol is modeled in combination with other organelles contained within the plasma membrane, such as mitochondria and plastids, which together form the cytoplasm. For simplicity, it is possible to idealize the plasma membrane, nuclear envelope, cytoplasm, nucleoplasm, and nucleolus as being of spheroidal shape. In various such embodiments, the plasma membrane may be modeled as a lipid bilayer composed of two regular layers of lipid molecules, in combination with the actin cytoskeleton providing mechanical strength as a membrane with a thickness of 10 nm. (See, e.g., Hine, R., 2005. The Facts on File Dictionary of Biology, 4th Edition. Vol. Facts on File Science Library. Checkmark Books, New York, the disclosure of which is incorporated herein by reference.) Similarly, embodiments model the nuclear envelope, a double lipid bilayer membrane, in combination with the nuclear lamin meshwork lending it structural support as a 20 nm thick membrane. In turn, the cytoplasm, nucleoplasm, and nucleolus may be modeled in embodiments as spheres with appropriate radii (e.g., 5.8 µm, 2.7 µm, and 0.9 µm), and subsequently scale them by a factor of 1.2 in two dimensions in order to obtain the desired spheroidal shape. In various embodiments an average nuclear diameter of about 5 µm may be used. (See, e.g., Cooper, G. M., 2000. The cell: A molecular approach, 2nd Edition. Sinauer Associates, Sunderland, Mass., USA, the disclosure of which is incorporated herein by reference.) Diameters for both cytoplasm and nucleolus follow from relevant studies (e.g., Lodish et al. and Guttman, the disclosures of which are cited above) that report nucleus-to-cell and nucleus-to-nucleolus volume ratios of 0.1 and 30.0, respectively.

Figure 3:
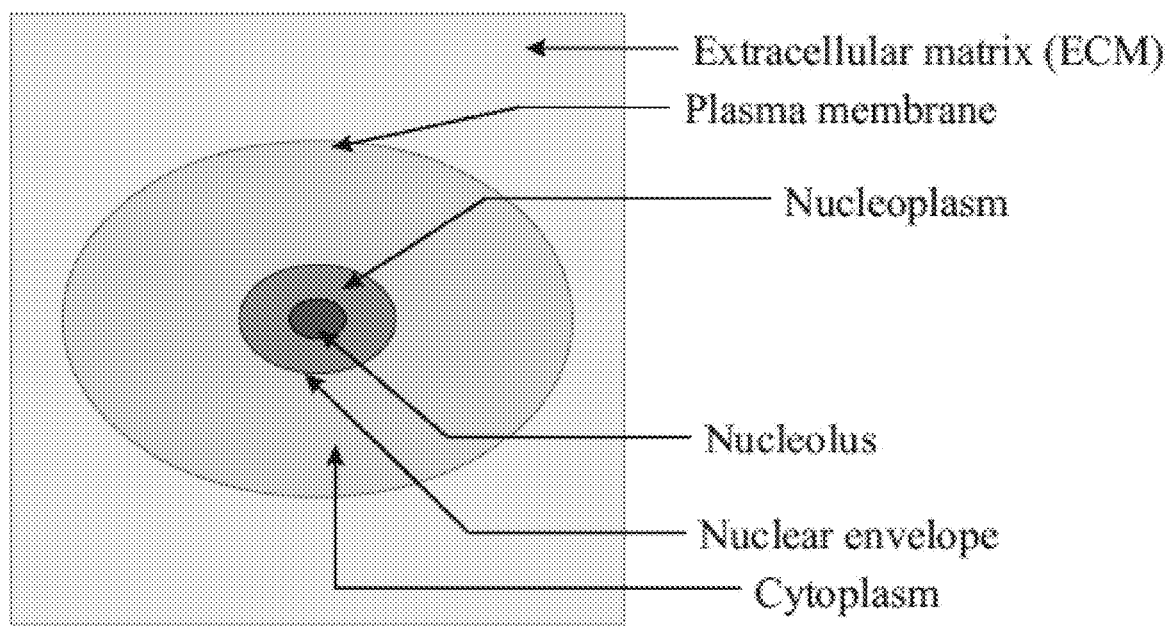
FIG. 3 provides a schematic diagram of a cell geometry with different cell constituents used in the methods in accordance with embodiments.

The geometry with all relevant cell constituents as used in finite element analyses in accordance with embodiments is illustrated in FIG. 3. In order to further elucidate the effect of an increasing nucleus-to-cell volume ratio, as observed experimentally, a range of geometries with increasing nuclear/nucleolar volumes are considered. (See, e.g., Berman, J. J., 2011. Precancer: The Beginning and the End of Cancer, 1st Edition. Jones & Bartlett Publishers, London, United Kingdom, the disclosure of which is incorporated herein by reference.) Regardless of geometry, in many embodiments the volume of the cytoplasm may be held fixed, and a constant nuclear-to-nucleolar volume ratio for both healthy and cancerous cells may be assumed. (See, e.g., Guttman and Halpern, cited above.) The different test geometries, according to embodiments, can therefore be designated by the nucleus-to-cell volume ratio n/c, whereby the value of n/c=1.0 then corresponds to the base geometry with parameters as listed above. For example, in such embodiments a nucleus-to-cell volume ratio of n/c=1.2 corresponds to a volume increase of both the nucleus and nucleolus of 20%.

Cell-to-cell differences and experimental uncertainties notwithstanding, observational evidence suggests that the cytoplasm, nucleus and nucleolus are ordered in the sense of increasing stiffness. Neglecting viscous effects, it is therefore possible, in accordance with embodiments, to model the elasticity of the different cell constituents by means of the Mooney-Rivlin-type strain energy density of the form:

$$W(F) = \frac{1}{2}\left[\mu_1\left(\frac{I_1}{J^{2/3}} - 3\right) + \mu_2 \frac{I_2}{J^{4/3}} + \kappa(J-1)^2\right] \quad \text{(EQ. 1)}$$

where F denotes the deformation gradient, $J=\det(F)$ is the Jacobian of the deformation, and $\mu_1$, $\mu_2$ and $\kappa$ are material parameters. (See, e.g., Kim, Y., et al., 2011. *Med. Biol. Engineering and Computing* 49 (4), 453-462, the disclosure of which is incorporated herein by reference.) For both cytoplasm and nucleus in cancerous cells, material parameters corresponding to the data reported in the literature are chosen and summarized in Table 1, below.

Although the above calculations may be used to estimate cell parameters for use in determining appropriate harmonic excitation frequencies, values for different geometric and material properties may also be obtained via suitable experimental measurements. It is additionally possible, in accordance with embodiments, to infer the elastic moduli of the nucleolus based on a comparison of the relative stiffnesses of the nucleoli and other nuclear domains. (See, e.g., Konno, K., et al., 2013. *IFMBE Proceedings*. Vol. 39. Springer, pp. 290-293, the disclosure of which is incorporated herein by reference.) For membrane elements of the plasma membrane and nuclear envelope, material parameters corresponding to the cytoplasm and nucleoplasm, respectively, may be chosen. Furthermore, matrix parameters may be inferred from the shear moduli reported for normal and fibrotic livers. (See, e.g., Schrader, J., et al., 2011. *Hepatology* 53 (4), 1192-1205, the disclosure of which is incorporated herein by reference.) For all parameters, it is possible to resort to small-strain elastic moduli conversions, with a Poisson's ratio of 0.49 to simulate a nearly incompressible material, in order to match experimental values with constitutive parameters. The stiffness of both cellular components and extracellular matrix (ECM) may be varied within a pathophysiologically-relevant range in order to investigate the effect of cell softening and ECM stiffening on eigenfrequencies. Finally, it is possible to assume both cytoplasm and nucleoplasm to have a mass density of 1 g/cm³, a value previously reported as an average cell density (see, e.g., Moran, U., et al., 2010. *Cell* 141, 1-2, the disclosure of which is incorporated herein by reference), and the density of the nucleolus to 2 g/cm³ (see, e.g., Birnie, G. D., 1976. Subnuclear Components: Preparation and Fractionation, 1st Edition. Butterworths Inc, Boston, Mass., the disclosure of which is incorporated herein by reference).

TABLE 1

Constitutive Cell Parameters

|  | K [kPa] | $\mu_1$ [kPa] | $\mu_2$ [kPa] |
| --- | --- | --- | --- |
| Plasma Membrane | 39.7111 | 0.41 | 0.422 |
| Cytoplasm | 39.7333 | 0.41 | 0.422 |
| Nuclear Envelope | 239.989 | 2.41 | 2.422 |
| Nucleoplasm | 239.989 | 2.41 | 2.422 |
| Necleolus | 719.967 | 7.23 | 7.266 |
| ECM | 248.333 | 5.0 | 5.0 |

Determining Estimate of Spectral Gap Between Target and Non-Target Free-Standing Cells In order to obtain a first estimate of the spectral gap between cancerous and healthy cells, according to embodiments, the eigenvalue problem of ellipsoidal cells embedded into the ECM may be used as an approximation. To this end, and in accordance with many such embodiments, cytoplasm, nucleoplasm and nucleolus may be discretized using linear tetrahedral elements, while linear triangular membrane elements are used for the plasma membrane and nuclear envelope.

Figure 4:
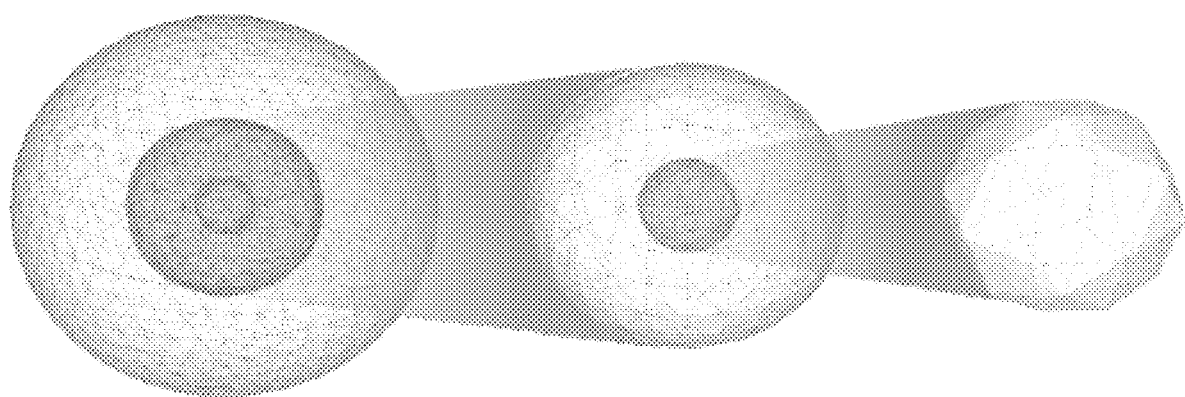
FIG. 4 provides a schematic diagram of a finite-element mesh of the plasma, cytoplasm, nuclear envelope, nucleoplasm and nucleolus in accordance with embodiments.

A typical finite element mesh, in accordance with various embodiments, for a cell geometry with a ratio of n/c=1 and a total of 40,349 elements is shown in FIG. 4. For the calculation of eigenfrequencies, meshes containing ~16,000 elements may be used for geometries ranging from a ratio of n/c=1 to n/c=2. As discussed in greater detail above, all cell constituents may be modeled by means of the hyperelastic Mooney-Rivlin model in accordance with embodiments, with the materials constants of Table 1.

Figure 5:
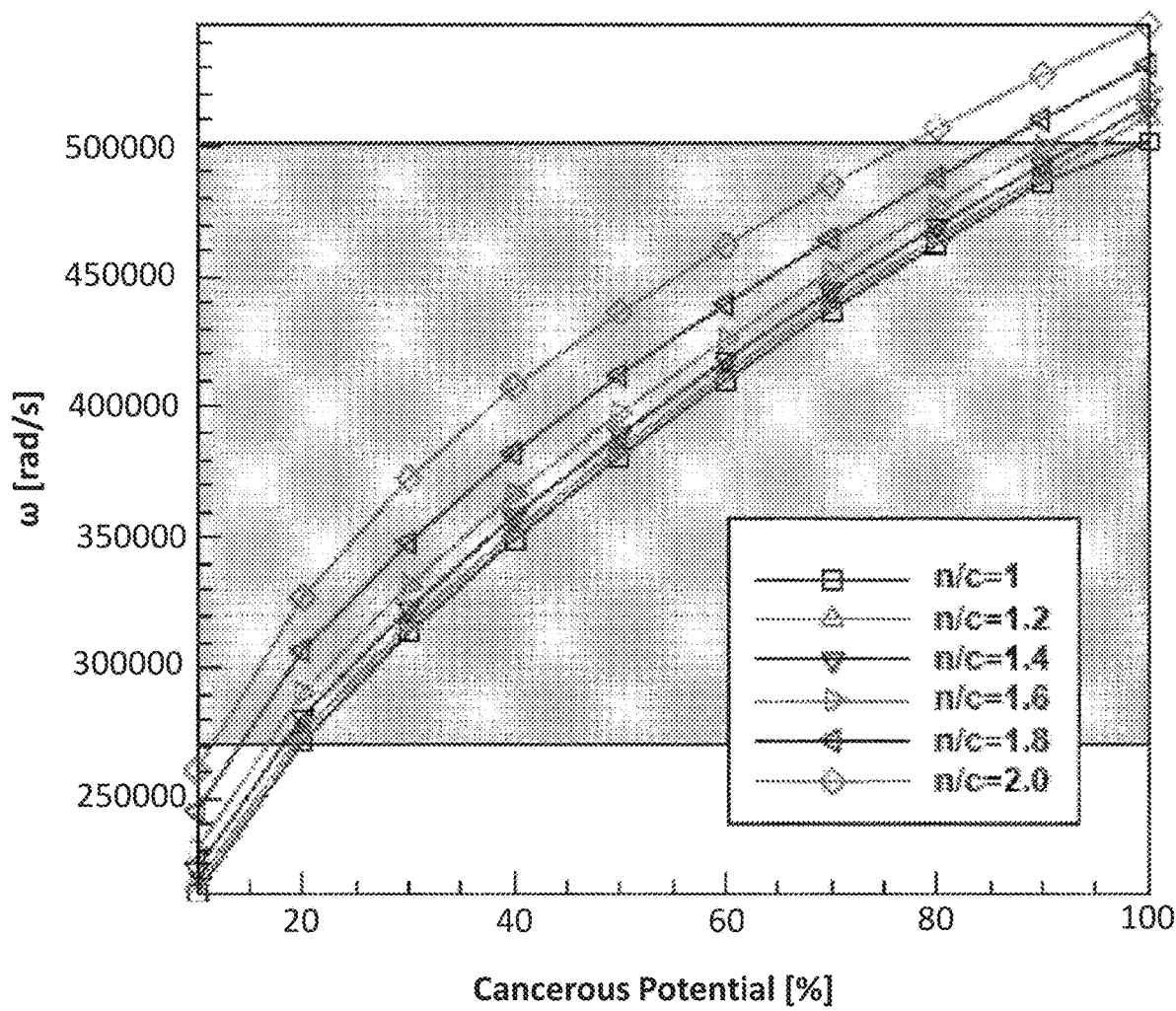
FIG. 5 provides a data graph of the lowest eigenfrequency for varying cell stiffness and increasing nucleolus/nucleoplasm-to-cytoplasm volume ratios n/c in accordance with embodiments.

FIG. 5 shows the calculated lowest eigenfrequency, rigid-body modes excluded, for different cell geometries and varying material properties, in accordance with embodiments. In accordance with many embodiments of the methods, the nucleolus/nucleoplasm-to-cytoplasm volume ratio is increased incrementally in the range of n/c=1.0 to n/c=2.0, resulting in six different test geometries. Since cancerous cells are more than 80% softer than healthy cells (Cross et al., cited previously), it is possible in accordance with embodiments to vary the elastic moduli in Table 1 within a pathophysiologically relevant range, with full values representing cancerous cells and increased moduli representing healthy cells. In addition, decreased elastic moduli of the extracellular matrix (ECM) are expected in healthy tissues (Schrader et al., previously cited). In many embodiments, a cancerous potential may be introduced as a scaling factor for the set of material properties of both cell constituents and extracellular matrix (ECM) according to the relation $$p_{Cell,varied} = p_{Cell} + (1-x) \cdot p_{Cell} \qquad (EQ. 2)$$

and $$p_{ECM,varied} = x \cdot p_{ECM} \qquad (EQ. 3)$$

where p denotes material parameters $\kappa$, $\mu_1$ and $\mu_2$, and a cancerous potential of 100% corresponds to values presented in Table 1.

FIG. 5 summarizes the calculated lowest eigenfrequency for different percentages of the parameter values presented in Table 1. Thus, a cancerous potential of 80% reflects an increase in elastic moduli of 20% for material parameters of the different cell constituents with a simultaneous decrease in elastic moduli of the ECM by 20%. The shaded area in FIG. 5 illustrates a typical gap in the lowest natural frequency for a nucleolus/nucleoplasm-to-cytoplasm volume ratio of n/c=1.0, with $\omega$=501,576 rad/s for cancerous cells and $\omega$=27,764 rad/s for a reduction in cancerous potential by 80%, the expected value for healthy cells. (Cross et al., previously cited.) An even higher spectral gap is recorded by additionally taking the growth in nucleolus/nucleoplasm-to-cytoplasm volume ratio into account, as experimentally observed in cancerous cells. (Berman, previously cited.) From these observations, it can be seen that in many embodiments a main determining factor responsible for the observed higher eigenfrequencies of cancerous tissues is the ECM, which is characterized by an increased stiffness.

A more detailed comparison of the spectra of healthy and cancerous cells, corresponding to cancerous potentials of 20% and 100%, respectively, is presented in Table 2, which collects the computed lowest ten eigenfrequencies for a cell geometry with volume ratio n/c=1.0. From this table it can be observed that cancerous cells have a ground eigenfrequency of the order of 500,000 rad/s, whereas healthy cells have a ground eigenfrequency of the order of 270,000 rad/s, or a healthy-to-cancerous spectral gap of the order of 230,000 rad/s. Accordingly, in many embodiments the harmonic excitation can be set based on these frequencies and frequency gap ranges to ensure that the energy produces destructive lysis inducing resonance in the cancerous cells and not in the healthy cells.

As shown in Table 2, the higher eigenfrequencies of the healthy cells may overlap with the ground eigenfrequency of cancerous cells. Therefore, special attention is required to examine whether or not excitation of cancerous cells might trigger healthy cells to resonate. Indeed, figures of merit other than natural frequency, including growth rates of resonant modes and energy absorption, may also be used in accordance with embodiments to play a role in differentiating the response of cancerous and healthy cells. These additional figures of merit are described in greater detail below.

TABLE 2

Comparison of Lowest Eigenfrequencies

|  | $\omega_1$ [rad/s] | $\omega_2$ [rad/s] | $\omega_3$ [rad/s] | $\omega_4$ [rad/s] | $\omega_5$ [rad/s] |
| --- | --- | --- | --- | --- | --- |
| Cancerous | 501576 | 502250 | 508795 | 532132 | 537569 |
| Healthy | 271764 | 274171 | 364259 | 364482 | 367413 |

|  | $\omega_6$ [rad/s] | $\omega_7$ [rad/s] | $\omega_8$ [rad/s] | $\omega_9$ [rad/s] | $\omega_{10}$ [rad/s] |
| --- | --- | --- | --- | --- | --- |
| Cancerous | 538512 | 557291 | 667107 | 678287 | 678771 |
| Healthy | 375570 | 376000 | 380063 | 424226 | 425327 |

Figure 6:
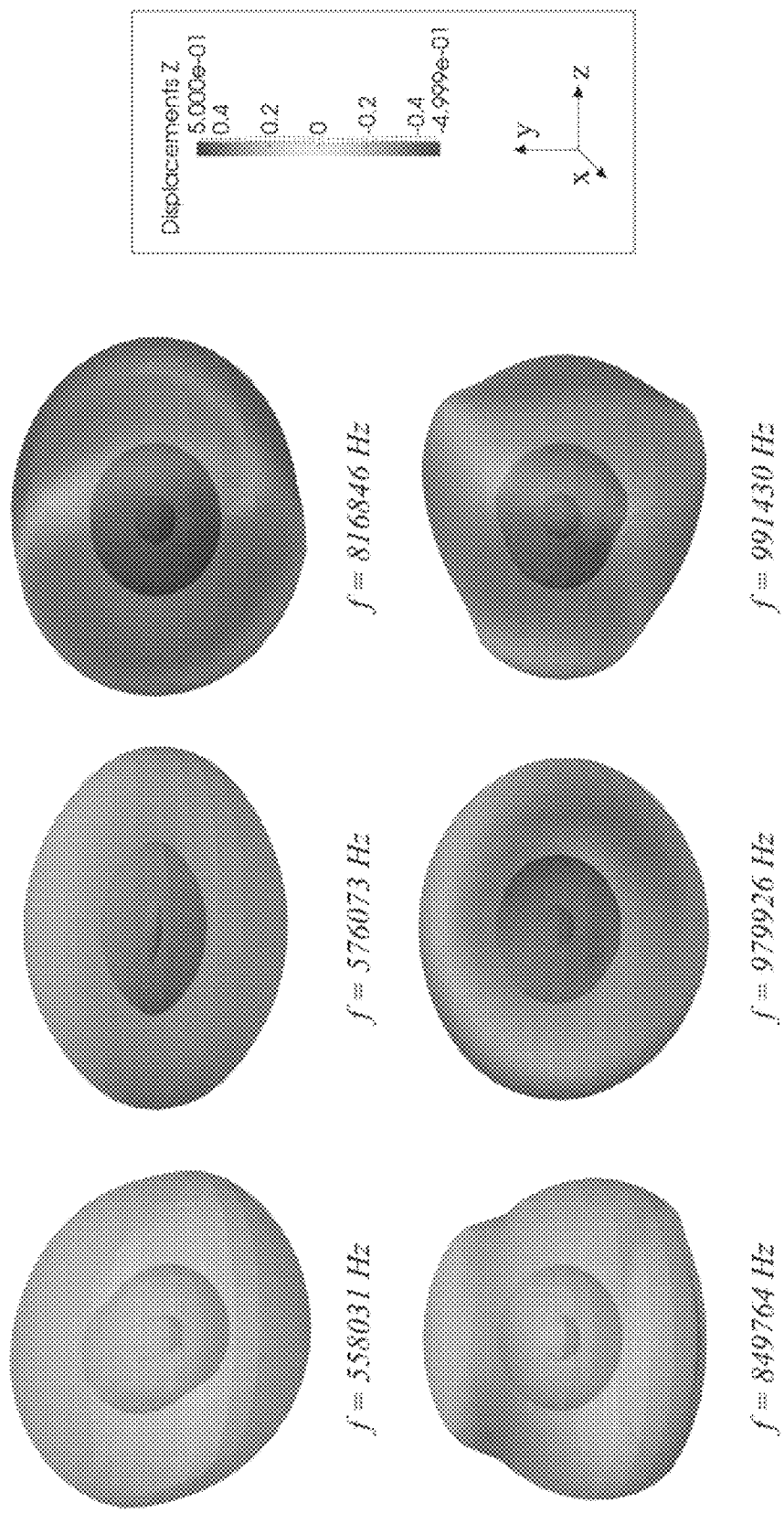
FIG. 6 provides diagrams of eigenmodes corresponding to different resonance frequencies for a ratio of n/c=1.0 and a cancerous potential of 100% in accordance with embodiments.

The eigenmodes described correspond to different embodiments of resonance frequencies for a ratio of n/c=1.0 and a cancerous potential of 100%. These eigenmodes are shown in FIG. 6. It may be noted from the figure how each mode represents different characteristic deformation mechanisms of the various cell constituents. Knowledge of the precise modal shape, as may be determined by imaging, may therefore be used in accordance with embodiments to target lysis of specific cell components. Thus, for example, in many embodiments shear deformation may be expected to dominate at a frequency of 558,031 rad/s, whereas volumetric deformations may be expected to be dominant at 576,073 rad/s. Accordingly in various embodiments these differences in deformation mode may be used to target specific cell constituents for lysis, such as the plasma membrane at a frequency of 816,846 rad/s.

Determining Spectral Gap for Periodic Arrangement of Cells

Figure 7:
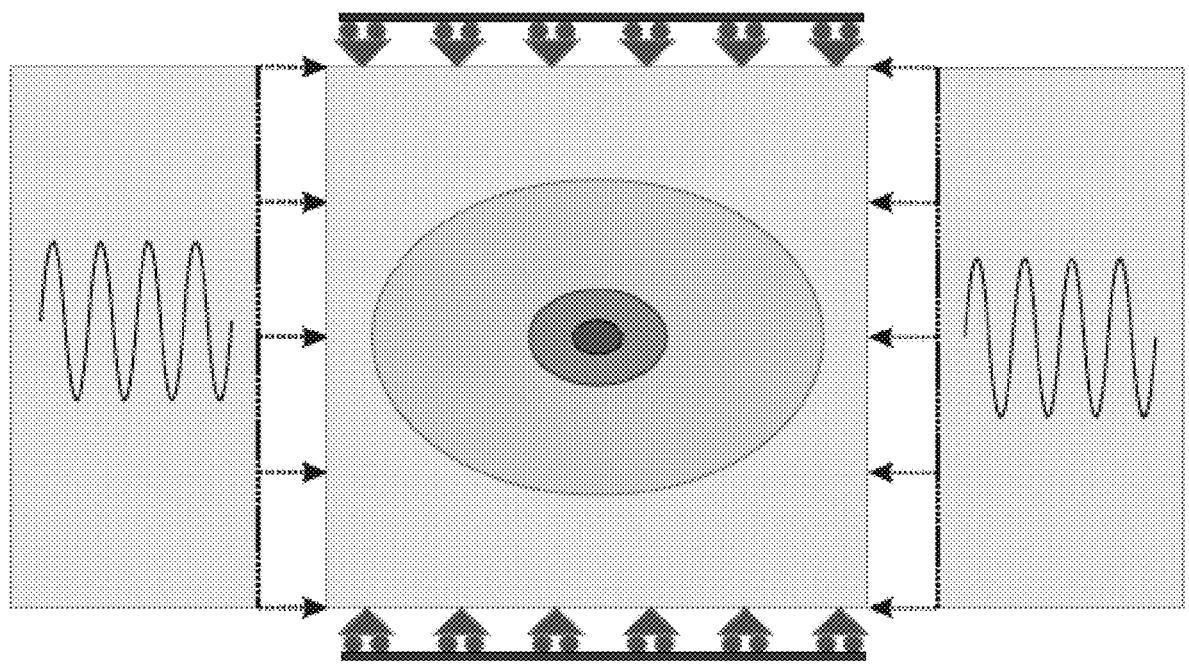
FIG. 7 provides a schematic diagram of a model displacement elastodynamic boundary value problem with applied harmonic excitation in accordance with embodiments.

The preceding embodiments of spectral harmonic excitation modes for free-standing cells can be extended to a tissue consisting of cells embedded into an extracellular matrix. In these embodiments, the analysis can be carried out by recourse to standard Bloch wave theory. Within this framework, the displacement field is assumed to be of the form:

$$u(x) = \hat{u}(x) e^{ik \cdot x} \qquad (EQ. 4)$$

where k is the wave vector of the applied harmonic excitation and the new unknown displacement field $\hat{u}(x)$ is defined within the periodic cell, as shown schematically in FIG. 7. (Bloch, F., 1929. Zeitschrift fur Physik 52, 555-600, the disclosure of which is incorporated herein by reference.) By periodicity, the values of wave vector k can be restricted to the Brillouin zone of the periodic lattice. Substitution of representation (EQ. 4) into the equations of motion results in a k-dependent eigenvalue problem. Accordingly, in many embodiments the corresponding eigenfrequencies $\omega_i(k)$ can be used to define the dispersion relations of the tissue. Details of implementation of Bloch-wave theory in elasticity and finite-element analysis may be found, for example, in Krodel, S., et al., 2013. *Advanced Engineering Materials* 15 (9999), 1-7, the disclosure of which is incorporated herein by reference.

Figure 8:
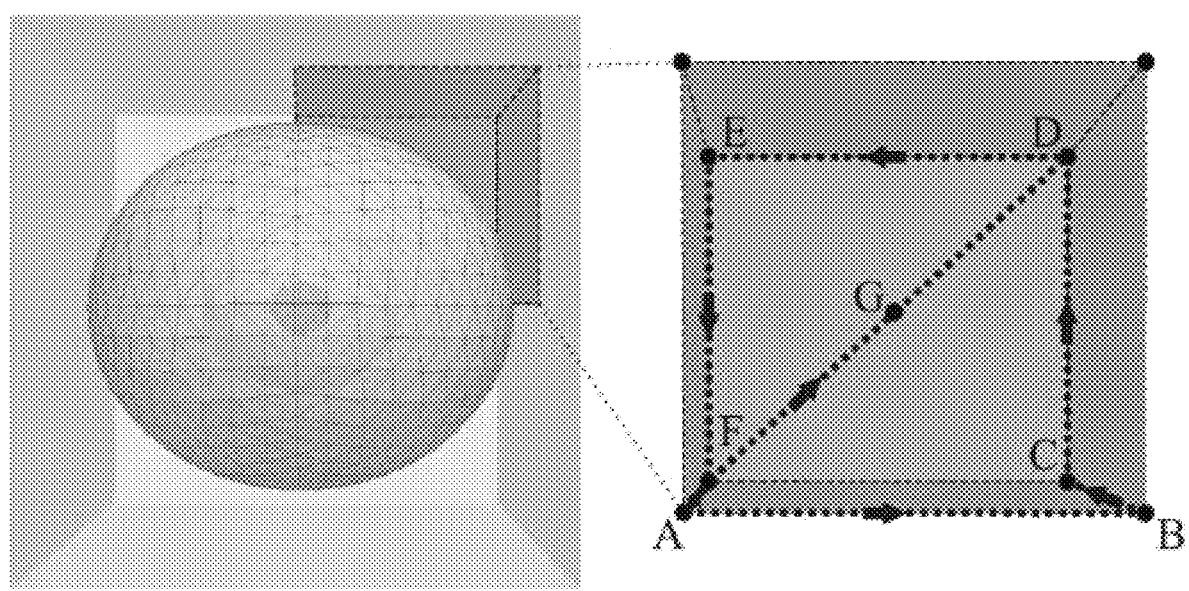
FIG. 8 provides a schematic diagram of the first irreducible Brillouin zone (left) and chosen k-path (right) in accordance with embodiments.
Figure 9:
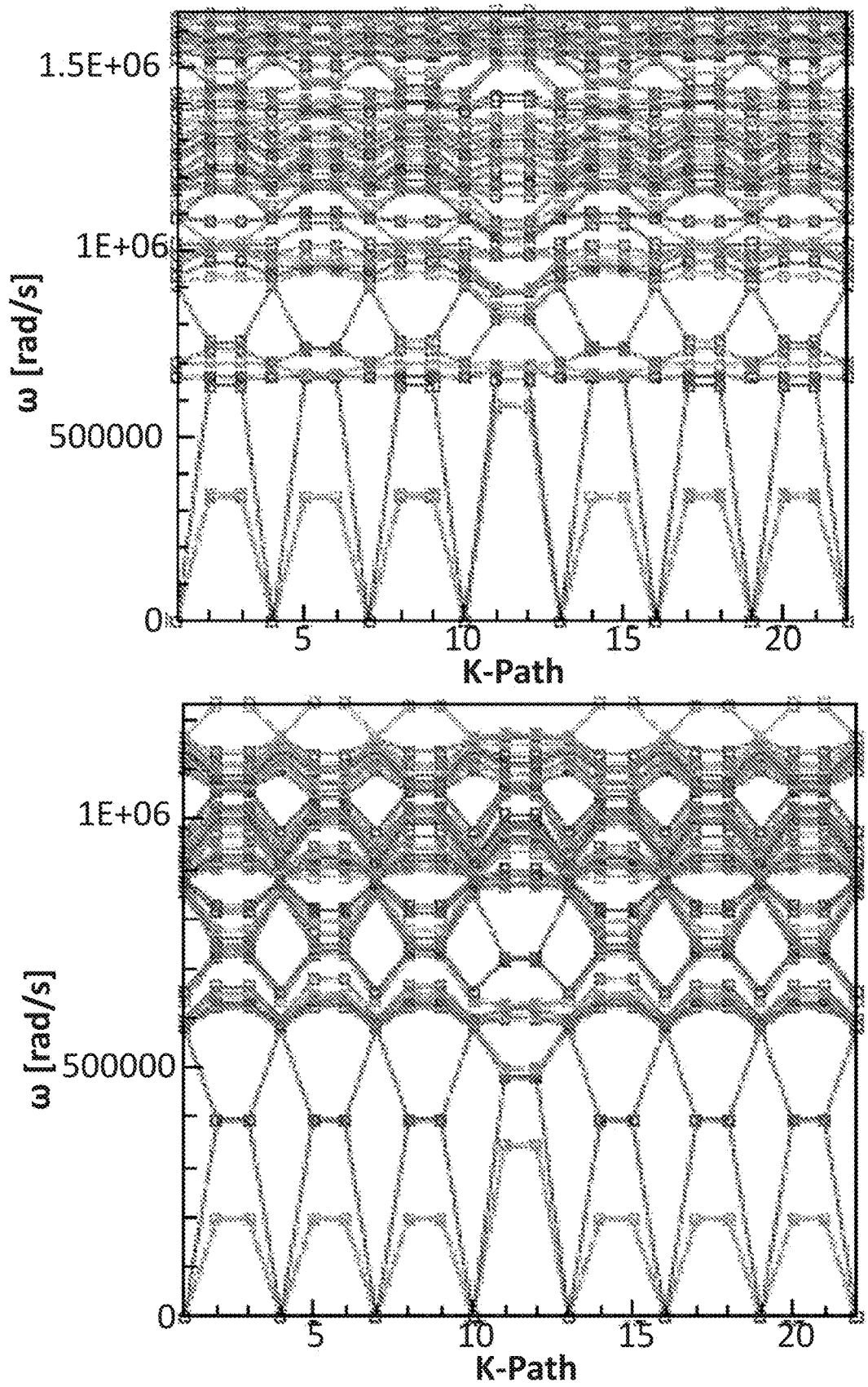
FIG. 9 provides diagrams of dispersion relations, whereby the k-path is traversed with a refinement of two points between neighboring nodes, whereas: (top) is for a cancerous cell, and (bottom) is for healthy cells, in accordance with embodiments.

In various embodiments then, it is possible to consider a cubic unit cell of size a=15 µm and the finite element discretization shown in FIG. 4. The extracellular matrix (ECM), not shown in the figure, is also discretized into finite elements. FIG. 8 shows the first irreducible Brillouin zone, which is itself a cube of size 2π/a. In order to visualize the dispersion relations, many embodiments choose the k-path along the edges and specific symmetry lines of the Brillouin zone also shown in FIG. 8. The path allows for the elliptical shape of the cells, with only one symmetry axis. The computed dispersion relations for both cancerous and healthy cells then follow as shown in FIG. 9, for the lowest 50 eigenfrequencies. Using the methods described in accordance with embodiments, it can be determined that the lowest eigenfrequencies of the healthy tissue are shifted uniformly towards lower values with respect to the eigenfrequencies of the cancerous tissue, with significant spectral gaps of the order of 200,000 rad/s between the two.

As discussed above, methods demonstrate that the computed ground eigenfrequency of free-standing cancerous cells is of the order of w~500,000 rad/s. In addition, from the properties of Table 1 it may be expected that a cancerous-tissue shear sound speed of the order of:

$$c = \sqrt{\frac{\mu}{\rho}} = \sqrt{\frac{3\kappa(1-2\nu)}{2\rho(1+\nu)}} \quad \text{(EQ. 5)}$$

where c~0.8 m/s (for cytoplasm) and c~7.2 m/s (for nucleolus). Therefore, at resonance the corresponding wave number of the applied harmonic excitation is of the order of k~w/c 725,000 rad/m (for cytoplasm) and k~69,444 rad/m (for nucleolus) or, correspondingly, a wavelength of the order of $\lambda \sim 2\pi/k \sim 10^{-5}$ m (for cytoplasm) and $\lambda \sim 9 \cdot 10^{-5}$ m (for nucleolus), which is larger than a typical cell size. Accordingly, in many embodiments the regime of interest is the long-wavelength regime, corresponding to the limit of k→0 in the preceding Bloch-wave analysis. Consequently, many embodiments utilize this limit, and the corresponding boundary value problem, which takes the form sketched in FIG. 7 and consists of the standard displacement elastodynamic boundary value problem with harmonic displacement boundary conditions applied directly to the boundary.

TABLE 3

Comparison of Growth Rate Ratios

| $\omega_n$ [rad/s] | 501576 | 502250 | 532132 | 537569 |
|---|---|---|---|---|
| $r_{n,cancerous}$ | $8.862 \cdot 10^6$ | $9.179 \cdot 10^6$ | $-3.898 \cdot 10^8$ | $-2.863 \cdot 10^7$ |
| $\omega_n$ [rad/s] | 496165 | 496165 | 519049 | 545277 |
| $r_{n,healthy}$ | $-3.882 \cdot 10^6$ | $-3.882 \cdot 10^6$ | $-2.032 \cdot 10^6$ | $-0.335 \cdot 10^6$ |

Relative Energy Absorption During Oncotripsy

As described in the above embodiments, the spectral gap, or gap in the lowest eigenfrequencies, between healthy and cancerous cells and tissues provides a first hint of sharp differences in the response of healthy and cancerous tissue to harmonic excitation. In particular, the preceding analysis shows that the fundamental frequencies of the cancerous tissue may be in close proximity to eigenfrequencies of the healthy tissue. Although this may appear to undermine the objective of selective excitation of the cancerous tissue, a complete picture requires consideration of the relative energy absorption characteristics and growth rates of resonant modes. To this end, the modal decomposition of the displacement field is considered, where:

$$U(t) = \Sigma_{n=1}^N u_n(t) \hat{U}_n \quad \text{(EQ. 6)}$$

where $(\hat{U}_n)_{n=1}^N$ are eigenvectors obeying the orthogonality and normalization condition and $(u_n(t))_{n=1}^N$ are time-dependent modal amplitudes obeying the modal equations of motion:

$$\ddot{u}_n(t) + \omega_n^2 \mu_n(t) = \hat{U}_n^T F_{ext}(t) = F_n(t) \quad \text{(EQ.7)}$$

In this equation, $\mu_n$ is the corresponding eigenfrequency, $F_{ext}(t)$ is the external force vector and $F_n(t)$ is the corresponding modal force. For a harmonic excitation of frequency $\omega_{ext}$, (EQ. 7) further specializes to:

$$\ddot{u}_n(t) + \omega_n^2 \mu_n = F_n \cos \omega_{ext} t \quad \text{(EQ.8)}$$

where $F_n$ is a constant modal force amplitude. At resonance, $\omega_{ext} = \omega_n$, the amplitude of the transient solution starting from quiescent conditions grows linearly in time and the transient solution follows as:

$$\mu_n(t) = \frac{F_n}{2\omega_n} t \sin(\omega_n t) \quad \text{(EQ. 9)}$$

It can thus be concluded that the growth rate of resonant modes is:

$$r_n = \frac{F_n}{2\omega_n} \quad \text{(EQ. 10)}$$

Figure 10A:
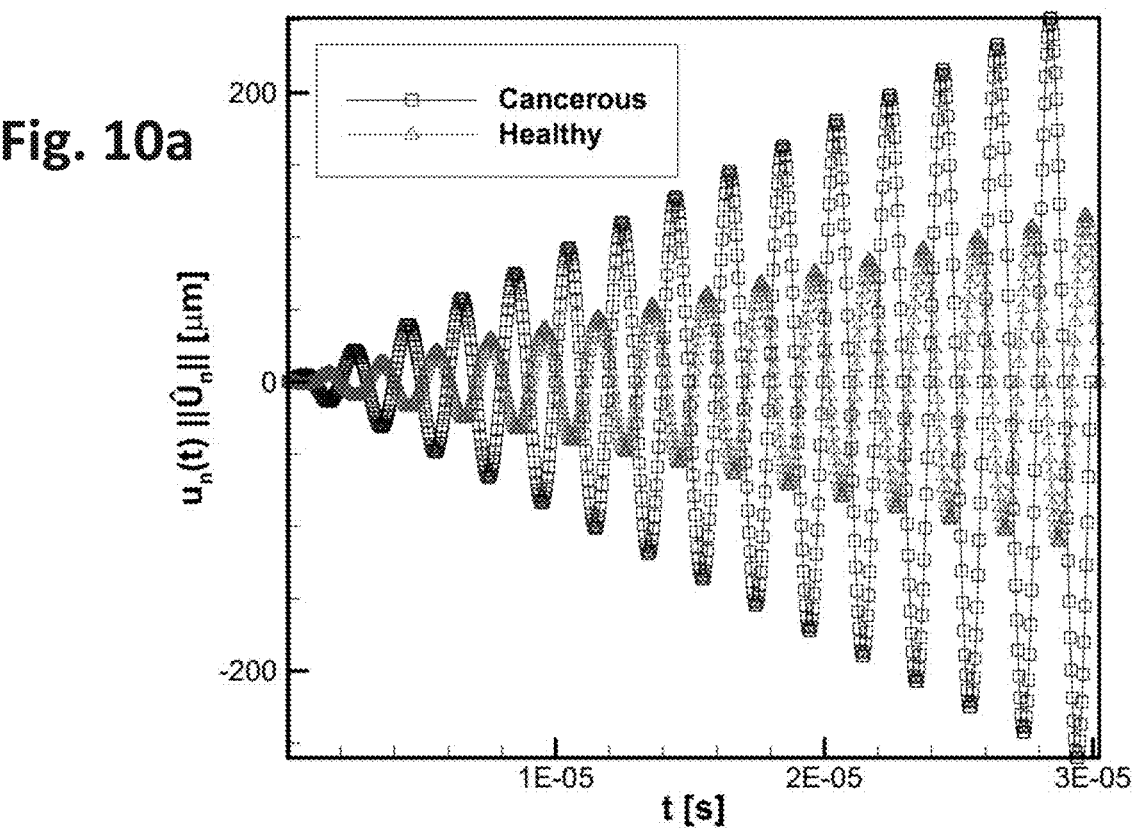
FIGS. 10a and 10b provide data graphs comparing $u_n$ during transient response simulations in the linearized kinematics framework for: (a) a cancerous cell with a cancerous potential of 100%; and (b) a healthy cell with a cancerous potential of 20% excited in accordance with embodiments.
Figure 10B:
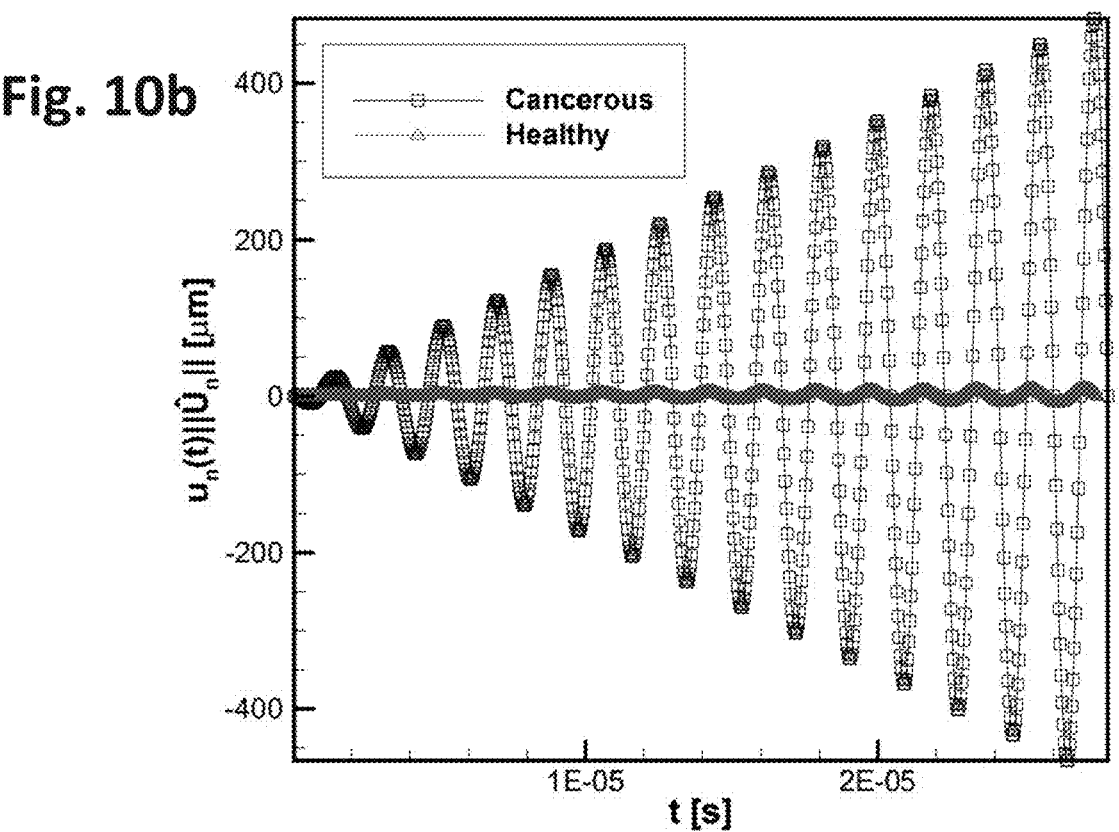

The growth rate $r_n$ can now be used in embodiments to characterize the behavior of cancerous cells excited at their resonance frequency $\omega_c$ relative to the behavior of healthy cells, which may have a neighboring eigenfrequency $\omega_h$. FIGS. 10a to 10b show the growth properties of $r_n$ for two different cases. In the first case (shown on the left), a cancerous cell is excited at its resonant frequency of $\omega_c$=501,576 rad/s, whereas the healthy cell is excited at its closest resonance frequency of $\omega_h$=496,165 rad/s. In the second case (shown on the right), eigenfrequencies of 538,512 rad/s and 545,277 rad/s are investigated. Both test cases reveal that the growth rate of the resonant response of the cancerous cells is much faster (and thus the deformation $u_n$ is much larger) than that of the healthy cells, which opens a window for selectively targeting the former, in accordance with various embodiments.

Summary of Cell Targeting Methods

In accordance with embodiments oncotripsy methods, allow for the identification of aberrations in the material properties and morphology of diseased cells (e.g., cancerous cells) in order to target them selectively by means of ultrasound radiation. It has been shown that the size difference between normal nuclei, with an average diameter of 7 to 9 microns, and malignant nuclei, which can reach a diameter of over 50 microns, constitutes an important criterion for malignancy. (See, e.g., Berman, previously cited). In addition, the material response of live metastatic cancer cells has been found to be more than 80% softer than that of healthy cells (Cross et al., previously cited), and cancer cells with the highest invasion and migratory potential have been found to be up to five times softer than healthy cells. (See, e.g., Swaminathan, V., et al., 2011. *Cancer Research* 71 (15), 5075-5080, the disclosure of which is incorporated herein by reference.) Conversely, experimental investigations on hepatocellular carcinoma cells (HCC) have revealed that an increase in stiffness of the extracellular matrix (ECM) promotes HCC cell proliferation (Schrader et al., previously cited) and advances malignant growth (Levental et al., previously cited). Since the stiffness of the nucleolus is higher than that of other nuclear domains (Houchmandzadeh, B., et al., 1997. *J. Cell Biol.* 139, 1-12; Caille, N., et al., 2002. *J. Biomech.* 35, 177-178; and Konno, et al., previously disclosed, the disclosure of which is incorporated herein by reference) with a simultaneous increase in mass density (Handwerger, K. E., et al., 2005. *Mol Biol Cell* 16 (1), 202-211, the disclosure of which is incorporated herein by reference), nuclei and nucleoli act as local resonators within cells that are subjected to harmonic excitation. Owing to the aforementioned aberrations in material properties and morphology, the eigenfrequencies at which local resonance occurs differ between healthy and cancerous cells, may be identified and exploited in accordance with embodiments.

In other embodiments additional factors may be taken into account in developing the model of cell resonance including, for example, the cytoskeletal tensegrity structure. Moreover, extensions of the cell membrane and cytoskeleton material model to account for strain-softening and damage may be used to provide insights into the failure mechanism induced by resonance. In various other embodiments, phase-field models may be used as a tool for building additional features into the calculations.

In addition, and as will be described in greater detail below, the effect of viscoelasticity on oncotripsy may be further investigated by taking varying viscoelastic parameters of different model constituents into account. To that end, in various embodiments viscoelastic constitutive models may be employed and target eigenfrequencies in the viscoelastic regime determined by performing frequency sweeps around eigenfrequencies calculated in the linear elastic framework.

In summary, while many of the simulations described herein are based on an idealized cell geometry of spheroidal shape wherein the cytosol is modeled in combination with other organelles contained within the plasma membrane, however, data and techniques may be implemented to explicitly account for individual organelles to enhance the predictiveness of the methods. Although the methods rely on idealized models, as shown in the accompanying data, the unavailability of complete experimental datasets for specific cell types does not prevent the identification of suitable harmonic excitation conditions for oncotripsy. Furthermore, as described above, unknown elements concerning specific cell types may be compensated by consideration of uncertainty and variability in cellular and extracellular material properties, in accordance with embodiments. In short, the lysis and fragmentation of cells subjected to resonant harmonic excitation in accordance with embodiments may be accomplished even without complete geometrical and anatomical models across a variety of cell types given the identification of the parameters identified herein.

Exemplary Embodiments

In this section several examples of systems and methods for determining harmonic excitation frequencies for performing oncotripsy and for performing oncotripsy on target cells are provided. In addition, the performance of several embodiments of the systems and methods are provided. The person skilled in the art will recognize that additional embodiments according to the invention are contemplated as being within the scope of the foregoing generic disclosure, and no disclaimer is in any way intended by these non-limiting examples.

Example 1: Verification of Cell Model

Based on the elastic model of the cell described in the foregoing, embodiments allow for the computation of the normal modes of vibration for use in oncotripsy for both healthy and cancerous cells using finite elements. The current exemplary embodiments provide methods to assess the accuracy of the finite element model used in subsequent calculations by means of comparisons to exact solutions. In one example a single spherical cell is considered and compared to numerically computed eigenmodes with the analytical solution (e.g., Kochmann, D. M., Drugan, W. J., 2012. *Proc. R. Soc. A,* 1-25, the disclosure of which is incorporated herein by reference) for an elastic sphere with an elastic spherical inclusion.

In the harmonic range, the finite-element discretization of the model, in accordance with embodiments, leads to the standard symmetric linear eigenvalue problem:

$$(K-\omega^2 M)\hat{U}=0 \quad \text{(EQ. 11)}$$

where K and M are the stiffness and mass matrices, respectively, $\omega$ is an eigenfrequency of the system and U is the corresponding eigenvector, subject to the normalization condition:

$$\hat{U}^T M \hat{U} = 1 \quad \text{(EQ. 12)}$$

For the spherical geometry under consideration, the modal analysis may be carried out analytically in closed form using (e.g., Kochman and Drugan, previously cited). For the homogeneous sphere, it is found that the natural frequencies $\omega_i$ follow as the roots of the function:

$$f(y) = \tan h\, y - \frac{y}{1-ky^2} \quad \text{(EQ. 13)}$$

with $$y = \sqrt{\frac{\rho\omega^2 b^2}{\lambda+2\mu}} \quad \text{and} \quad k = \frac{\lambda+2\mu}{4\mu} \quad \text{(EQs. 14 \& 15)}$$

where b is the outer radius and $\lambda$ and $\mu$ are the Lame' constants. Furthermore, analytic solutions have been reported for an isotropic linear-elastic spherical inclusion of radius $\alpha$, moduli $\lambda_1$ and $\mu_1$ within a concentric isotropic linear-elastic coating of uniform thickness of outer radius b, moduli $\lambda_2$ and $\mu_2$. In this case, the eigenfrequencies $\omega_i$ follow from the characteristic equation det A=0, where:

$$A_{11} = \frac{\cos(jx)}{jx} - \frac{\sin(jx)}{j^2 x^2},$$

$$A_{12} = \frac{\sin(jkx)}{j^2 k^2 x^2} - \frac{\cos(jkx)}{jkx},$$

$$A_{12} = -\frac{\cos(jkx)}{j^2 k^2 x^2} - \frac{\sin(jkx)}{jkx},$$

$$A_{21} = 0,$$

$$A_{21} = 4k_2^2 \frac{\cos jk}{j^2 k^2} + \left(\frac{1}{jk} - \frac{4k_2^2}{j^3 k^3}\right)\sin(jk),$$

-continued $$A_{23} = 4k_2^2 \frac{\sin jk}{j^2k^2} + \left(\frac{1}{jk} - \frac{4k_2^2}{j^3k^3}\right)\cos(jk),$$

$$A_{31} = -k\left(4k_1^2 \frac{\cos jk}{j^2k^2} + \left(\frac{1}{jk} - \frac{4k_1^2}{j^3k^3}\right)\sin(jk)\right),$$

$$A_{32} = 4k_2^2 \frac{\cos(jkx)}{j^2k^2x^2} + \left(\frac{1}{jkx} - \frac{4k_2^2}{j^3k^3x^3}\right)\sin(jk),$$

$$A_{33} = 4k_2^2 \frac{\sin(jkx)}{j^2k^2x^2} + \left(\frac{1}{jkx} - \frac{4k_2^2}{j^3k^3x^3}\right)\cos(jk),$$

with dimensionless quantities:

$$k_1 = \sqrt{\frac{U^I}{\lambda^I + 2\mu^I}}, k_2 = \sqrt{\frac{\mu^{II}}{\lambda^{II} + 2\mu^{II}}} \quad \text{(EQ. 16)}$$

$$k = \sqrt{\frac{\lambda^I + 2\mu^I}{\lambda^{II} + 2\mu^{II}}}, j = \sqrt{\frac{\rho\omega^2 b^2}{\lambda^I + 2\mu^I}} \quad \text{(EQ. 18)}$$

and with x=a/b.

Table 3, below, provides a comparison between analytical and finite-element values of the fundamental frequency of a solid sphere and a sphere with a high-contrast spherical inclusion for the particular choice of parameters listed in Table 2, below. The finite-element values found in accordance with embodiments correspond with a mesh of ≈15,000 linear tetrahedral elements, representative of the meshes used in subsequent calculations. As shown from the tables, the finite-element calculations in accordance with embodiments result in harmonic excitation frequencies selective to a target cell to a ~$10^{-3}$ relative error.

TABLE 4

Geometric, Material & Constitutive Parameters

| Constitutive parameters | $K_1$ [Pa] | $\mu_1$ [Pa] | $K_2$ [Pa] | $\mu_2$ [Pa] |
|---|---|---|---|---|
| Solid sphere | 1.0 | 1.0 | 1.0 | 1.0 |
| Spherical inclusion | 1.0 | 0.1 | 1.0 | 0.1 |

| Material/geometric parameters | $P_1$ [kg/m³] | $P_2$ [kg/m³] | $r_{inner}$ [m] | $r_{outer}$ [m] |
|---|---|---|---|---|
| Solid sphere | $10^{-3}$ | $10^{-3}$ | 3 | 30 |
| Spherical inclusion | $10^{-3}$ | $10^{-3}$ | 3 | 30 |

TABLE 5

Lowest Radial Eigenfrequency from Analytical and Finite-Element Analysis

| Method | $\omega_{lowest}$ [rad/s] (I) | $\omega_{lowest}$ [rad/s] (II) |
|---|---|---|
| Analytical Solution | 3.72394 | 1.17402 |
| Finite Element Analysis | 3.71717 | 1.17547 |
| Relative Error (%) | 0.1871797 | 0.123507 |

In addition, to the accuracy assessment discussed above, the convergence of the finite-element model may be evaluated by considering five different meshes of 2,171; 3,596; 8,608; 11,121; and 15,215 elements. From this analysis, it is found that that the accuracy in the lowest eigenfrequency for the finest mesh in accordance with embodiments is of the order of 0.2%, which is sufficient to determine an appropriate range for harmonic excitation.

Example 2: Transient Response Analysis

Previously an analysis was described concerning embodiments for determining the resonant response of cells and tissues under harmonic excitation in the harmonic range during oncotripsy. In this example, confirmation and extension of the conclusions of the harmonic analysis are confirmed by carrying out fully nonlinear implicit dynamics simulations of the transient response of healthy and cancerous cells under resonant harmonic excitation.

In this example, a geometry of ratio n/c=1 is considered, as provided in FIG. 4, together with the material parameters of Table 1. Attention in this analysis is given to the long wavelength limit, i.e. to ultrasound radiation of wavelengths larger than the cell size. In keeping with this limit, harmonic displacement boundary conditions are enforced directly as shown in FIG. 3 in order to mechanically excite the cell. The strength of the harmonic excitation used in the calculations is $\hat{u}_0$=0.04 μm.

In the simulations, the transient amplification of the cell response is tracked up to failure. In the simulations it is assumed that failure occurs when the stress in the cytoskeletal polymer network, which constitutes the structural support for cell membranes, reaches a threshold strength value. Previous studies found that the macroscopic network strength can be traced to the microscopic interaction potential of cross-linking molecules and other cytoskeletal components such as actin filaments. (See, e.g., Lieleg, O., et al., 2009. *Biophysical Journal* 96, 4725-4732, the disclosure of which is incorporated herein by reference.) Here, a rupture strength of the order of 30 Pa is assumed based on strength values of a single actin/cross-linking protein bond. (Lieleg et al. previously cited.)

Figure 11:
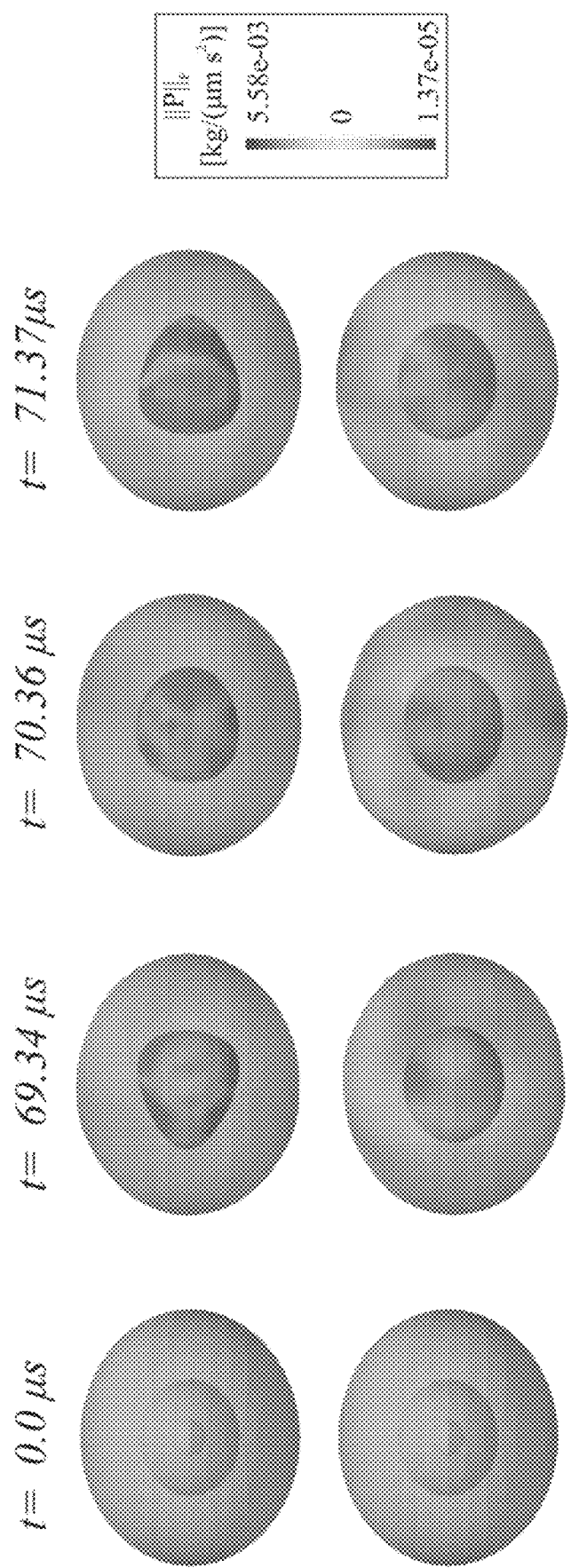
FIG. 11 provides diagrams of the transient response of a cancerous cell (top) and a healthy cell (bottom) at resonance for a ratio of n/c=1.0 and a cancerous potential of 100% in accordance with embodiments.
Figure 12A:
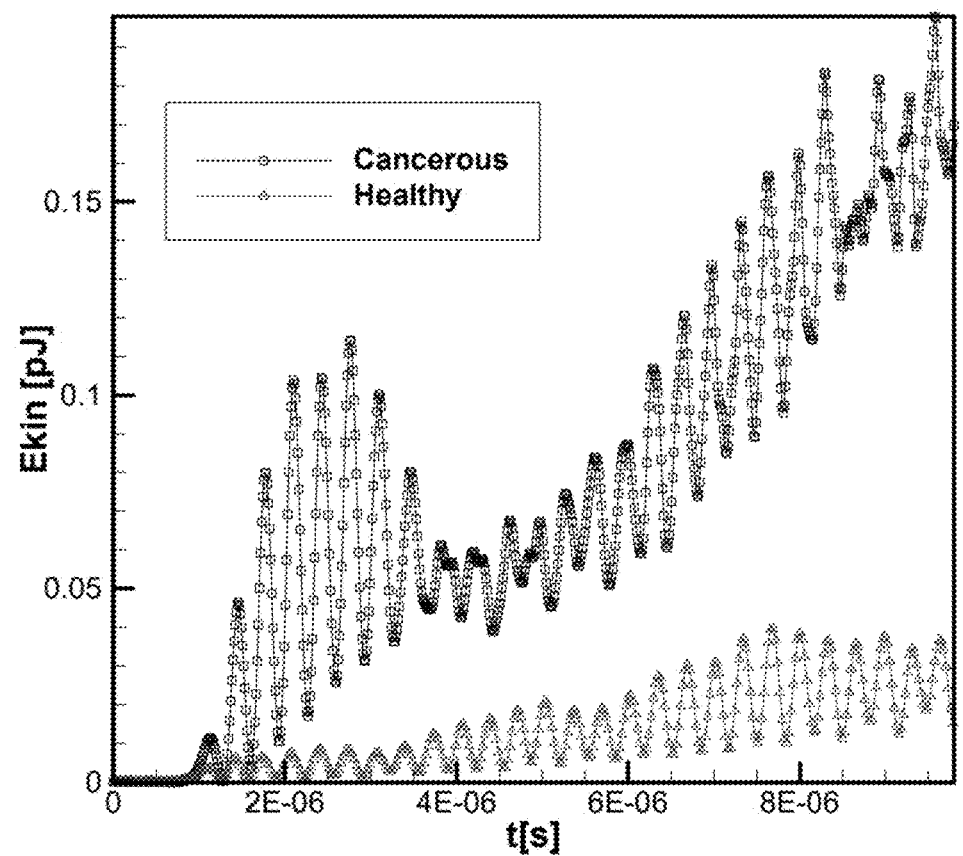
FIGS. 12a and 12b provide data graphs of: (a) kinetic energy; and (b) potential energy of the nuclear envelope during excitation at resonance of both healthy and cancerous cells in accordance with embodiments.
Figure 12B:
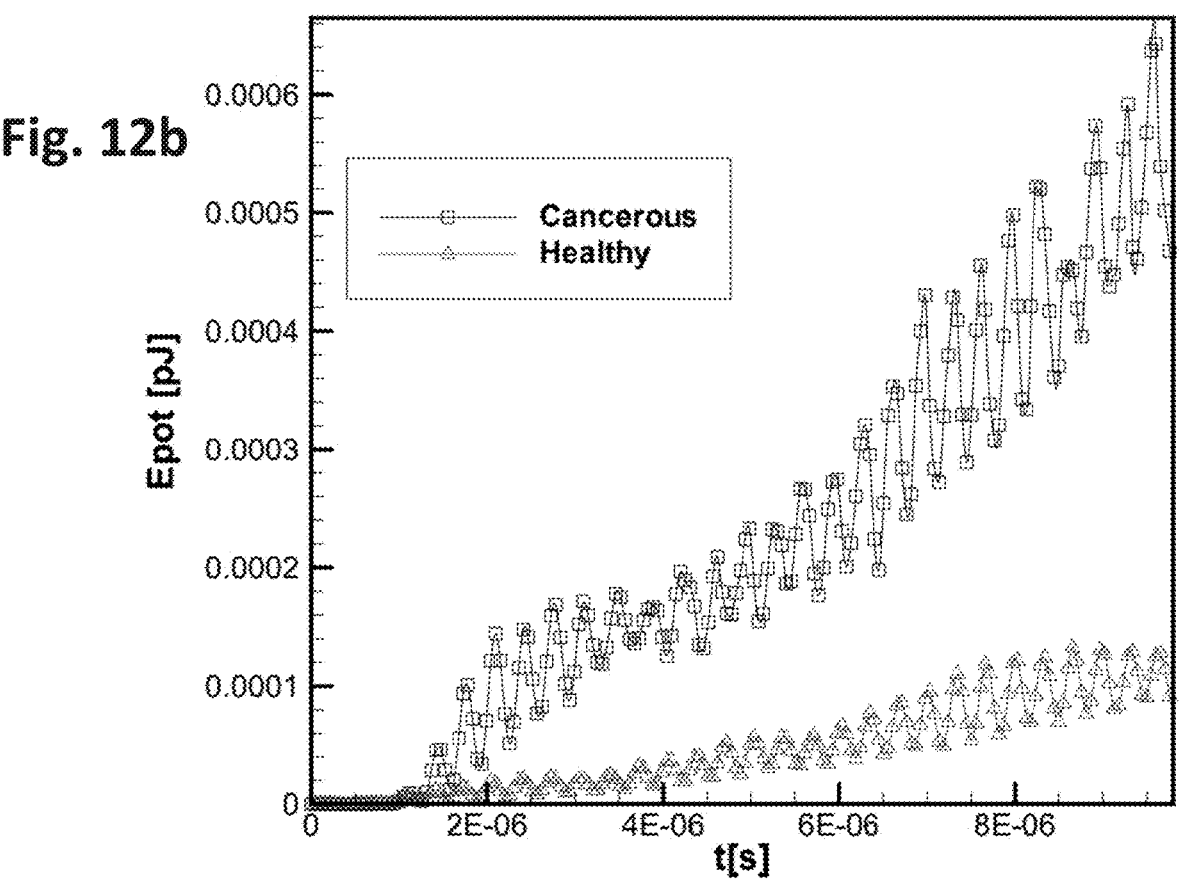

FIG. 11 shows the fully-nonlinear transient response of healthy and cancerous cells at the resonant frequency of the latter. It can be seen from the figure that stresses in both the plasma membrane and nuclear envelope of the cancerous cell grow at a much faster rate than in healthy cells. For the harmonic excitation under consideration, the strength of the nuclear envelope of the cancerous cell reaches the rupture strength at time $t_{lysis}$ 71s, while, at the same time, the level of stress in the healthy cells is much lower. FIGS. 12a to 12b furthermore illustrate the kinetic and potential energy of the nuclear envelope during excitation at resonance of both healthy and cancerous cells.

From transient response simulations, the energy that needs to be supplied until the point of rupture is reached is:

$$E_{lysis} = \int_{t=0}^{t_{lysis}} \int_{\delta\omega} t \cdot \dot{u} dS dt \approx \Sigma_{i=0}^{n_{lysis}} \Sigma_{j \in \delta\Omega} 1/2 (F_j(t_{i+1}) + F_j(t_i)) \cdot (u_j(t_{i+1}) - u_j(t_i)) \quad \text{(EQ. 19)}$$

where t is the applied traction on the boundary δω, u is the displacement vector, $F_j(t_i)$ is the force acting on surface node j at time $t_i$, and $u_j(t_i)$ is the corresponding displacement vector. For a cell geometry with a ratio of n/c=1.0 and a cancerous potential of 100%, calculations give a value of 228 pJ for the energy per cell required for lysis. Assuming an average cell size of 20 μm, a time to lysis of 70 μs and a tumor of 1 cm in size, this energy requirement translates into a power density requirement in the range of 0.8 W/cm².

Example 3: Confirmation of Oncotripsy Viability

As described, oncotripsy, in accordance with embodiments, provides means of selectively targeting cancer cells via resonant harmonic excitation. The method makes use of aberrations in material properties of cancerous cells which allow to induce local resonance up to membrane lysis in cancerous cells while leaving healthy cells intact. In this example the influence of viscoelasticity on the oncotripsy effect is explored. Based on Rayleigh damping, viscoelastic target frequencies are derived and used to simulate the fully nonlinear transient response of healthy and cancerous cells at resonance. Results confirm the viability of oncotripsy with viscoelastic material behavior of cell constituents accounted for.

Figure 13A:
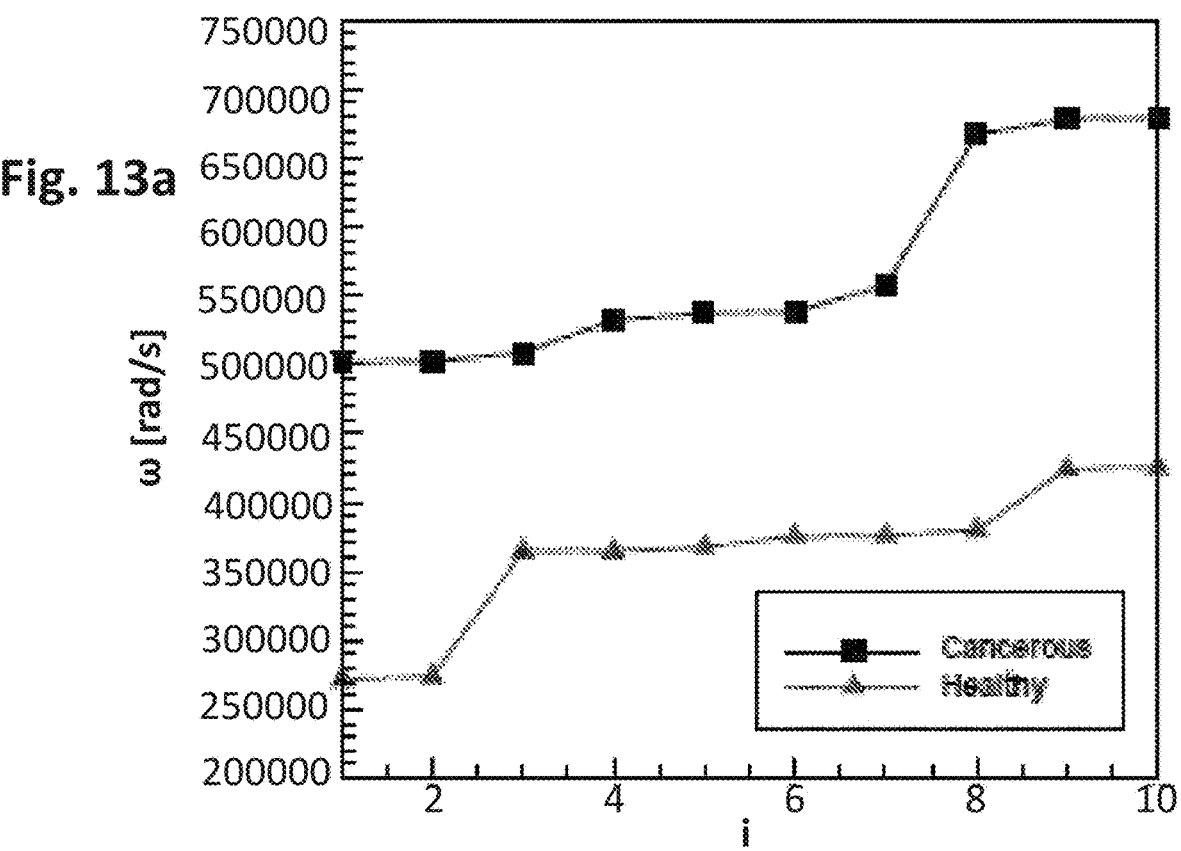
FIGS. 13a and 13b provide data graphs of eigenfrequencies calculated from the standard symmetric linear eigenvalue problem for comparison of the lowest ten eigenfrequencies between healthy and cancerous cells based on: (a) changes in material properties & (b) changed in material properties with nuclear/volume increase by 100% in accordance with embodiments.
Figure 13B:
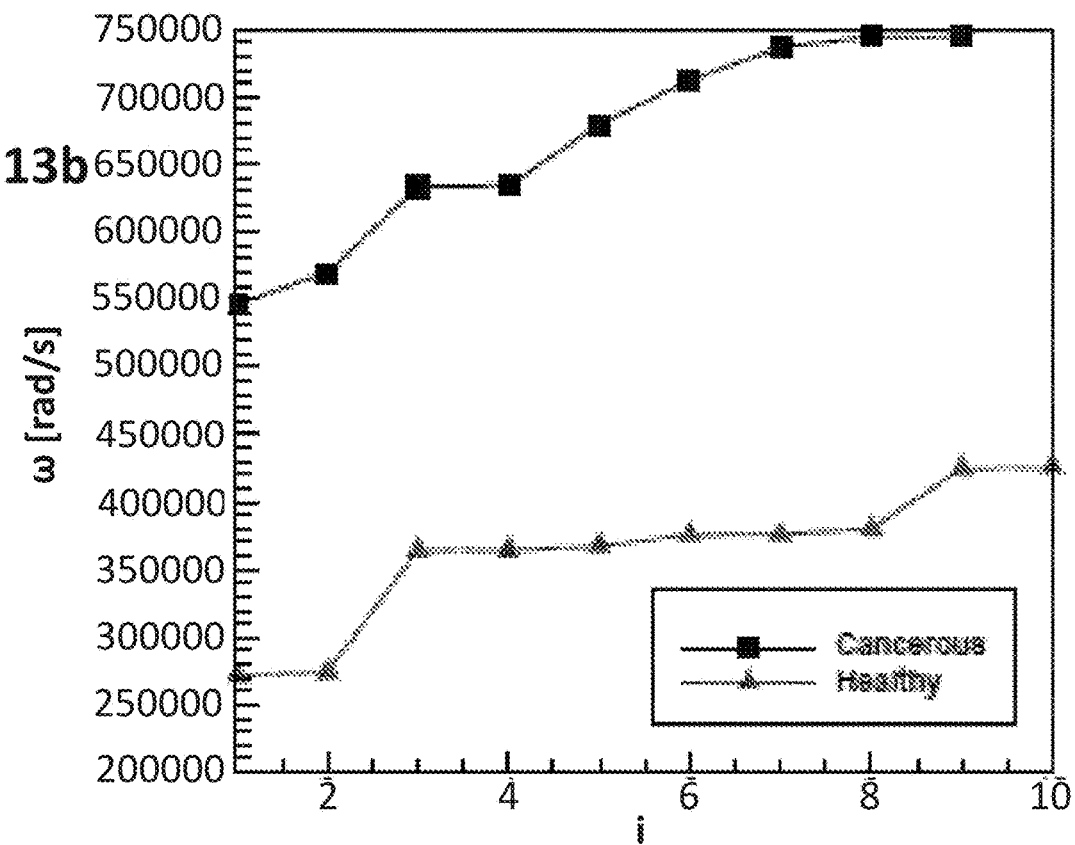

As described above, it has been shown in embodiments that cancerous eigenfrequencies lie above those of healthy cells, with a typical gap in the lowest natural frequency of about 229,812 rad/s, as shown in FIGS. 13a and 13b. It is also shown that the resonant growth rates of cancerous eigenfrequencies typically exceed those of healthy cells, an important requirement for selectively targeting cancerous tissues while leaving healthy cells (potentially possessing close neighboring eigenfrequencies) intact. In various embodiments, the main determining factor responsible for the observed higher eigenfrequencies of cancerous tissues is furthermore determined to be the extracellular matrix (ECM), due to its increased stiffness.

Figure 14:
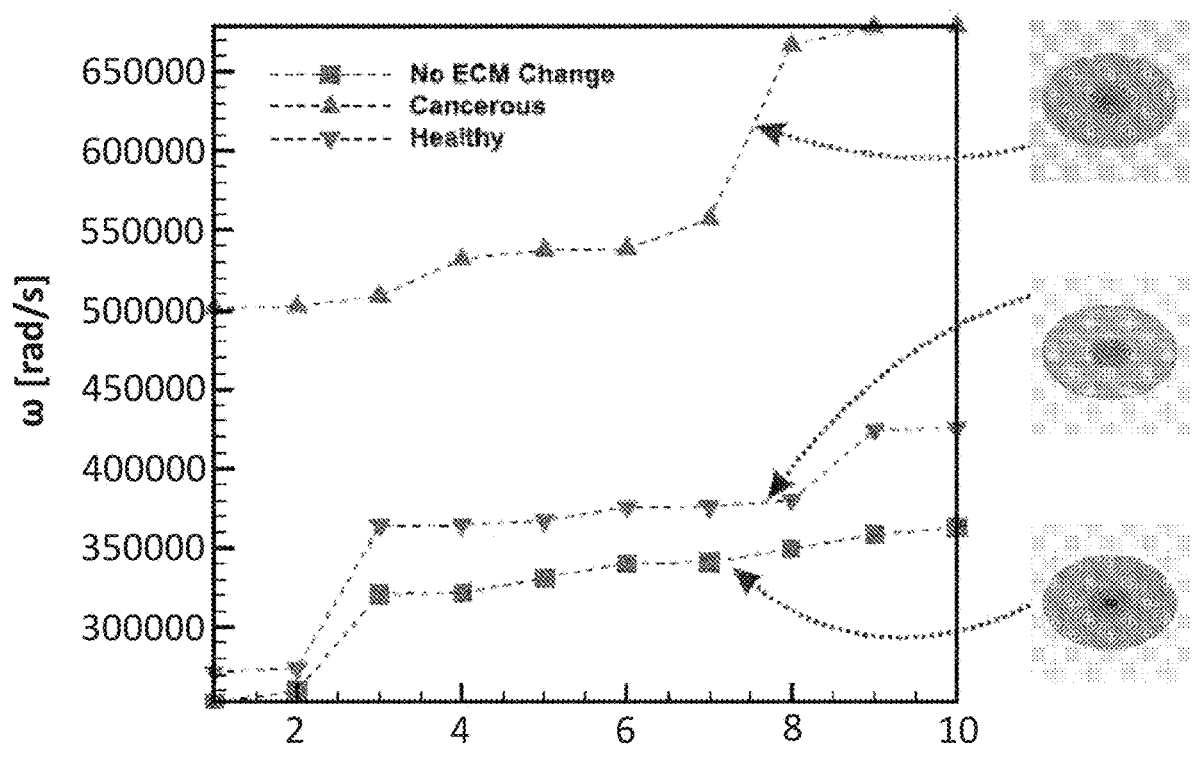
FIG. 14 provides a data graph showing the influence of the extracellular matrix on the lowest ten eigenfrequencies where from top to bottom they show: cancerous ECM/cancerous cell; healthy ECM/healthy cell; and healthy ECM/cancerous cells in accordance with embodiments.

FIG. 14, in turn illustrates that the eigenfrequencies of a cancerous/cancerous ECM/cell system lie above those of the healthy case, while the eigenfrequencies of the healthy/cancerous ECM/cell system are decreased. However, previous embodiments assume elasticity and neglect viscoelastic effects. In the present example, the influence of viscoelasticity on the oncotripsy effect is examined. Initially, the material parameters and geometrical model components used in the presented numerical study are determined, followed by a derivation of viscoelastic target frequencies and simulations of the fully nonlinear viscoelastic transient solution at resonance.

Cell Geometry and Material Parameters

Figure 15:
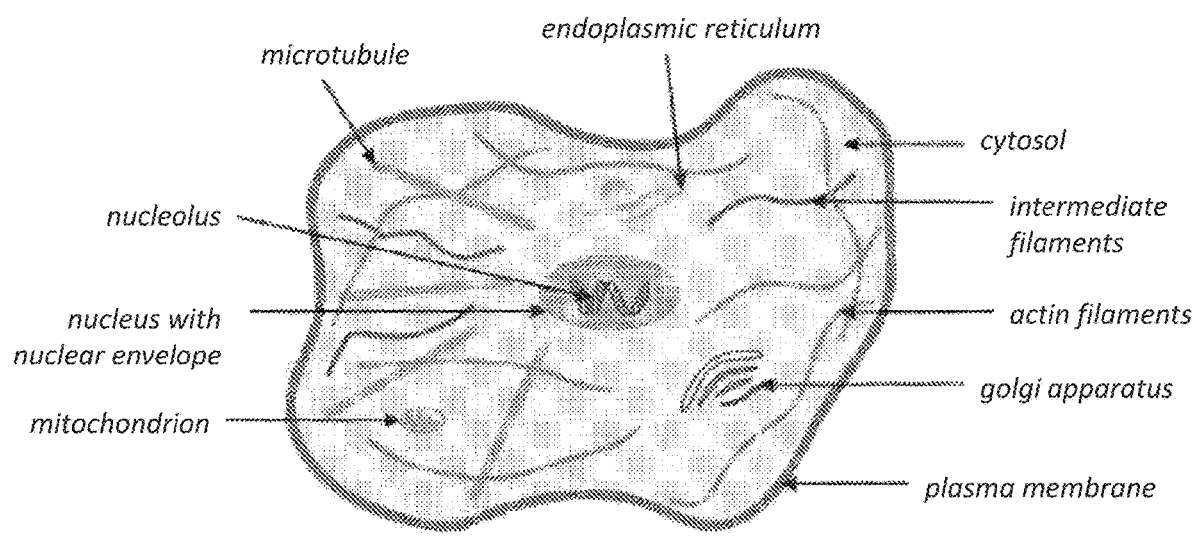
FIG. 15 provides a schematic diagram showing a eukaryotic cell with typical subcellular structures.

As previously discussed, in mammalian cells, the nucleus, as the largest cellular organelle, occupies about 10% of the total cell volume (Alberts et al., 2002 & Lodish et al., 2004, previously cited). It is surrounded by the cytosol, a viscous solid containing several subcellular structures such as the golgi apparatus, the mitochondrion, and the endoplasmic reticulum as illustrated in FIG. 15. The cytosol and other organelles contained within the plasma membrane, for instance mitochondria and plastids, form the so-called cytoplasm. The nucleus is bounded by the nuclear envelope and contains the nucleoplasm, a viscous solid similar in composition to the cytosol. It furthermore comprises the nucleolus, which constitutes the largest structure within the nucleus and consists of proteins and RNA.

Figure 16:
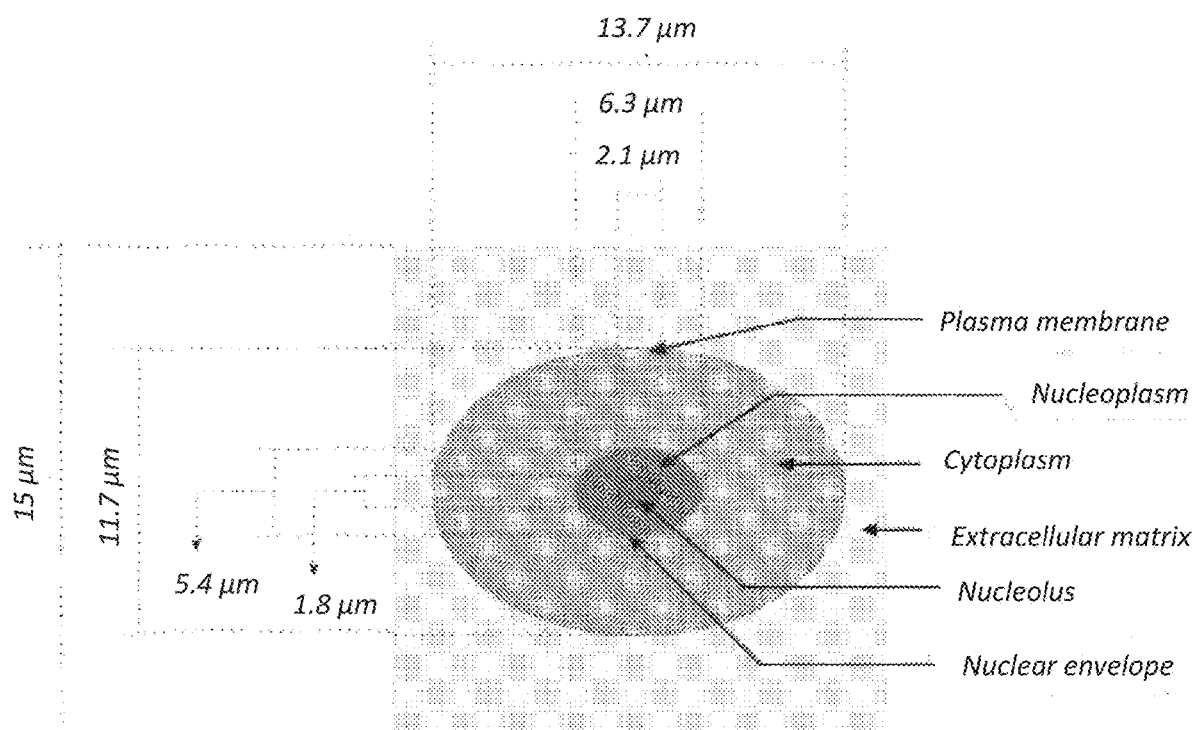
FIG. 16 provides a schematic diagram of an exemplary cell geometry with different cell constituents use in finite-element methods in accordance with embodiments.

The geometric model of the cells presented in this study takes into account the cytoplasm, nucleus and nucleolus, as well as the plasma membrane and nuclear envelope, FIG. 16. Each of the cell constituents is idealized to be of spheroidal shape, whereby the nucleolus, nucleoplasm and cytoplasm are defined as spheres with radii of 0.9 µm, 2.7 µm and 5.8 µm, respectively, and subsequently scaled by a factor of 1.2 in two dimensions. Measurements are based on an average nuclear diameter of 5 µm as reported in (Cooper, G. M., 2000. The cell: A molecular approach, 2nd Edition. Sinauer Associates, Sunderland, Mass., USA, the disclosure of which is incorporated herein by reference) and nucleus-to-cell as well as nucleus-to-nucleolus ratios (Guttman, P. H., Halpern, S., 1935. Am. J. Cancer 25, 802-806. & Lodish, H., et al., 2004. Molecular Cell Biology, 5th Edition. WH Freeman, New York, the disclosures of which are incorporated herein by reference.) The plasma membrane, a lipid bilayer composed of two regular layers of lipid molecules, is modeled as a membrane with a thickness of 10 nm. (See, e.g., Hine, R., 2005. The Facts on File Dictionary of Biology, 4th Edition. Vol. Facts on File Science Library. Checkmark Books, New York., the disclosure of which is incorporated herein by reference.) Similarly, the nuclear envelope, a double lipid bilayer membrane, is modeled as a membrane with a thickness of 20 nm.

Based on these parameters, in various embodiments the wavelength of the lowest eigenfrequency is expected to exceed cellular dimensions. For displacements on the order of the membrane thickness, curvatures below $10^{-2}$ are obtained. Accordingly, bending effects can be neglected to first order and model the plasma membrane and nuclear envelope by recourse to membrane elements. Finally, both the cytoplasm and nucleoplasm are assumed to have a mass density of 1 g/cm$^3$ (Moran et al., 2010, previously cited), whereas the density of the nucleolus is set to 2 g/cm$^3$ (Birnie, 1976, previously cited).

The elasticity of the different cell constituents is modeled in accordance with embodiments by means of a Mooney-Rivlin-type strain-energy density of the form:

$$W(F) = \frac{1}{2}\left[\mu_1\left(\frac{I_1}{J^{2/3}} - 3\right) + \mu_2\left(\frac{I_2}{J^{4/3}}\right) + \kappa(J - 1)^2\right] \quad \text{(EQ. 19)}$$

where $\mu_1$, $\mu_2$ and $\kappa$ are material parameters, F is the deformation gradient, J=det(F) denotes the Jacobian of the deformation and $l_1$=tr(C) and $l_2$=½(tr(C)$^2$−tr(C$^2$)) are the first and second invariants of the right Cauchy-Green tensor, respectively. Material parameters for the cytoplasm and nucleus are calibrated based on values reported in literature (e.g., Kim et al. (2011), previously cited, for hepatocellular carcinoma cells). In addition, constitutive parameters of the nucleolus are inferred from a comparison of the relative stiffnesses of the nucleoli and other nuclear domains (e.g., via Konno et al., 2013, previously cited) and matrix parameters are inferred from shear moduli of fibrotic livers presented in the literature (e.g., via Schrader et al. (2011), previously cited) by recourse to small-strain elastic moduli conversions with a Poisson's ratio of 0.49. The complete set of material parameters used in subsequent finite element simulations of cancerous and healthy cells in this example is summarized in Tables 6 and 7.

TABLE 6

Set of Constitutive Parameters

|  | K [kPa] | $\mu_1$ [kPa] | $\mu_2$ [kPa] |
| --- | --- | --- | --- |
| Plasma membrane | 39.7333 | 0.41 | 0.422 |
| Cytoplasm | 39.7333 | 0.41 | 0.422 |
| Nuclear envelope | 239.989 | 2.41 | 2.422 |
| Nucleoplasm | 239.989 | 2.41 | 2.422 |
| Nucleolus | 719.967 | 7.23 | 7.266 |
| ECM | 248.333 | 5.0 | 5.0 |

TABLE 7

Constitutive Parameters (based on stiffening of cell constituents)

|  | K [kPa] | $\mu_1$ [kPa] | $\mu_2$ [kPa] |
|---|---|---|---|
| Plasma membrane | 71.5199 | 0.738 | 0.7596 |
| Cytoplasm | 71.5199 | 0.738 | 0.7596 |
| Nuclear envelope | 431.98 | 4.338 | 4.3596 |
| Nuceloplasm | 431.98 | 4.338 | 4.3596 |
| Nucleolus | 1295.94 | 13.014 | 13.0788 |
| ECM | 198.666 | 4.0 | 4.0 |

To ensure that eigenfrequencies calculated in the discretized framework correspond to fully converged values, we consider five different meshes of 2,171; 3,596; 8,608; 11,121; and 15,215 linear tetrahedral elements. It is found that the accuracy in the lowest eigenfrequency for the finest mesh is of the order of 0.2%, which is sufficient for purposes of the embodiments.

Based on the finite element discretization of the model, it is possible to consider viscoelasticity of the Kelvin type, which results in the equation of motion:

$$M\ddot{U}+C\dot{U}+KU=F(U,t) \quad \text{(EQ. 20)}$$

where M, C and K are the mass, damping and stiffness matrices, respectively. Nodal displacements are represented in terms of a modal decomposition of the vector of all nodal displacements, namely, $$U(t)=\Sigma_{n=1}^{N} u_n(t)\hat{U}_n \quad \text{(EQ. 21)}$$

where the eigenvectors obey the orthogonality constraint:

$$\hat{U}_n \cdot M \hat{U}_n = 1 \quad \text{(EQ. 22)}$$

It is to be recalled that linear elastic eigenfrequencies and eigenmodes follow from the standard symmetric linear eigenvalue problem:

$$(K-\omega_n^2 M)\hat{U}=0 \quad \text{(EQ. 23)}$$

with the property that:

$$\hat{U}_n \cdot K \hat{U}_n = \omega_n^2 \quad \text{(EQ. 24)}$$

It is further possible to assume Rayleigh damping, corresponding to a damping matrix of the form:

$$C=\alpha M+\beta K \quad \text{(EQ. 25)}$$

where the term $\alpha M$ damps the lowest modes preferentially and $\beta K$ damps highest modes preferentially (Cook et al., previously presented). Conveniently, the modal equations of motion decouple as:

$$\ddot{u}_n+(\alpha+\beta\omega_n^2)\dot{u}_n+\omega_n^2 u_n=F_n(t) \quad \text{(EQ. 26)}$$

Assuming modal forces of the form:

$$F_n(t)=\hat{F}_n e^{i\Omega t} \quad \text{(EQ. 27)}$$

with viscoelastic circular frequency, we have $u_n=\hat{u}_n e^{i\Omega t}$. Using these relations and solving for the nodal displacements, it is possible to obtain:

$$\hat{u}_n = \left( \frac{\omega_n^2 - \Omega^2}{(\omega_n^2 - \Omega^2)^2 + (\alpha + \beta\omega_n^2)^2 \Omega^2} - i \frac{\alpha + \beta\omega_n^2}{(\omega_n^2 - \Omega^2)^2 + (\alpha + \beta\omega_n^2)^2 \Omega^2} \right) \hat{F}_n \quad \text{(EQ. 28)}$$

whence the amplitude of nodal displacements follows as:

$$|\hat{u}|=\sqrt{\Re(\hat{u}_n)^2+\Im(\hat{u}_n)^2} \quad \text{(EQ. 29)}$$

Equation (29) can be used, in accordance with embodiments, to determine viscoelastic circular frequencies at which to irradiate the cancerous cell, thus maximizing the oncotripsy effect. The damping parameters $\alpha$ and $\beta$ from dynamic atomic force microscopy (AFM) experiments on live fibroblast cells presented in, for example Cartagena and Raman (2014). (See, Cartagena, A., Raman, A., 2014. *Biophysical Journal* 106, 1033-1043, the disclosure of which is incorporated herein by reference.) A comparison of EQ. 26 with their single-degree-of-freedom equation of motion governing the cantilever tip motion in the AFM experiments gives the relation:

$$\frac{\omega_n}{Q_{far}} = \alpha + \beta\omega_n^2 \quad \text{(EQ. 30)}$$

where $Q_{far}$ is the quality factor far from the sample surface, related to the phase:

$$\tan(\Phi_{1far})=\sqrt{4_{far}^{-2}}-2 \quad \text{(EQ.31)}$$

Using measurements of $\Phi_{1far}$ at the boundary of the frequency range of interest gives $\alpha=1139.70$ s$^{-1}$ and $\beta=9.92\times 10^{-6}$ s.

Figure 17A:
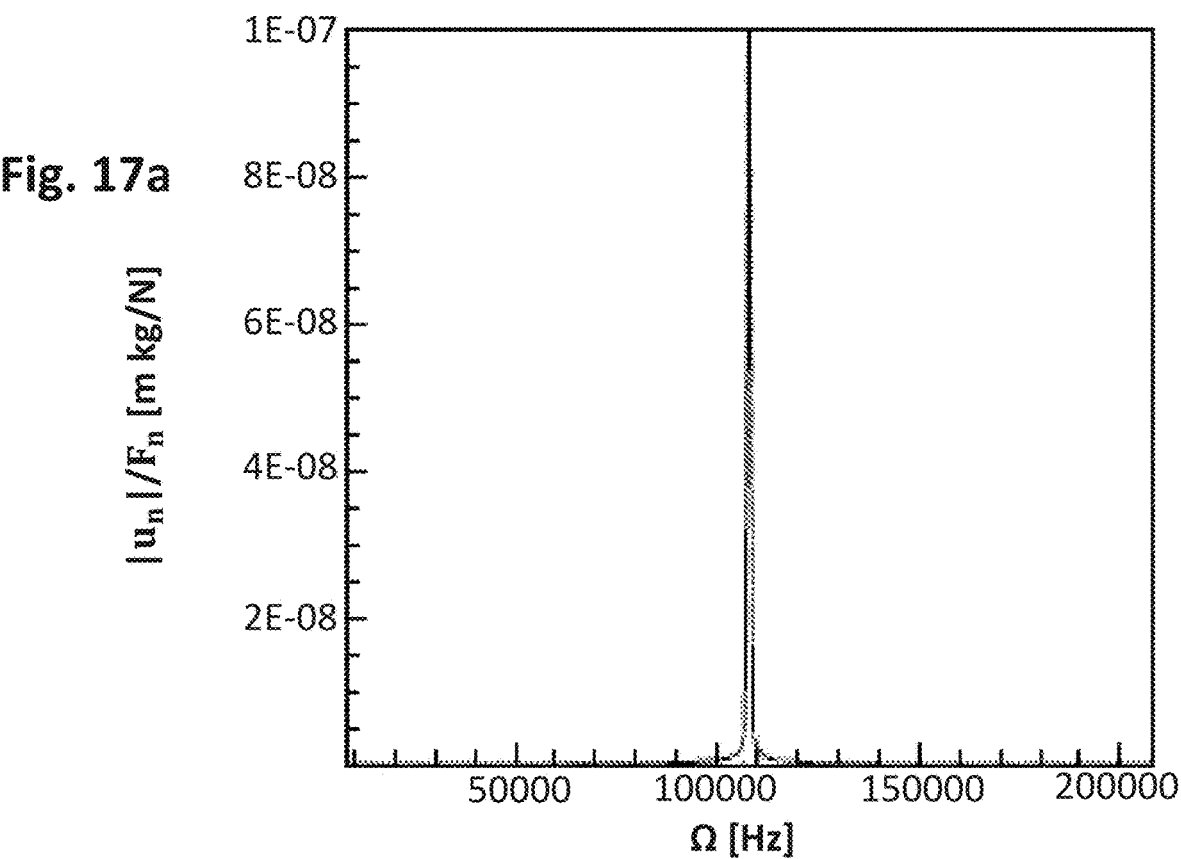
FIGS. 17a and 17b provide data graph showing the displacement amplitude factor as a function of driving frequency in accordance with embodiments where: (a) is with no damping; and (b) is with damping.
Figure 17B:
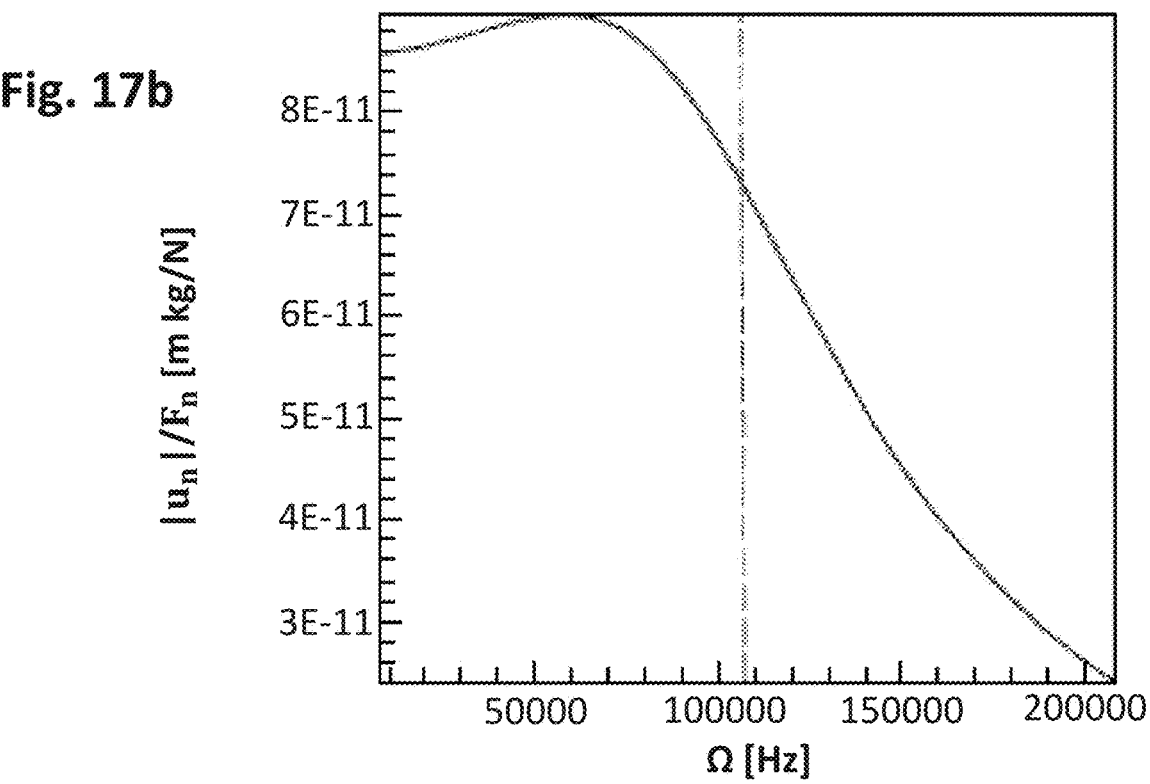

FIG. 17a shows a plot of the displacement amplitude vs. the driving frequency in the absence of damping. As expected, the displacement amplitude diverges at resonance with the natural frequency. The corresponding plot for damping is shown in FIG. 17b, where the damped eigenfrequency $\omega_n$ is also shown for reference. As expected, the displacement amplitude peaks at driving frequencies somewhat lower than $\omega_1$. Table 8 additionally compares the ten lowest eigenfrequencies in the damped and undamped cases. In all cases, the viscoelastic natural frequencies lie somewhat below the undamped natural frequencies $\omega_n$. From these results it can be concluded that viscoelasticity may be expected to have a modest effect on the natural frequencies and resonant growth rates of cancerous cells.

TABLE 8

Comparison of Ten Lowest Eigenfrequencies in Damped & Undamped Cases

|  | $\omega_1$ [1/s] | $\omega_2$ [1/s] | $\omega_3$ [1/s] | $\omega_4$ [1/s] | $\omega_5$ [1/s] |
|---|---|---|---|---|---|
| Elastic | 79828.3 | 79935.6 | 80977.2 | 84691.4 | 85556.8 |
| Viscoelastic | 62193.1 | 62224.2 | 62512.5 | 63333.0 | 63475.1 |

|  | $\omega_6$ [1/s] | $\omega_7$ [1/s] | $\omega_8$ [1/s] | $\omega_8$ [1/s] | $\omega_{10}$ [1/s] |
|---|---|---|---|---|---|
| Elastic | 85706.8 | 88695.6 | 106173 | 107953 | 108030 |
| Viscoelastic | 63497.7 | 63822.4 | 59538.4 | 58305.2 | 58247.5 |

It is noted that viscoelastic target frequencies calculated from EQ. (29) are based on previously determined linear elastic eigenfrequencies $\omega_1$, which follow from the standard symmetric linear eigenvalue problem (EQ. 23) in the discretized framework. Damping parameters $\alpha$ and $\beta$ therefore act upon the combined ECM/cell system in the present example.

Figure 18A:
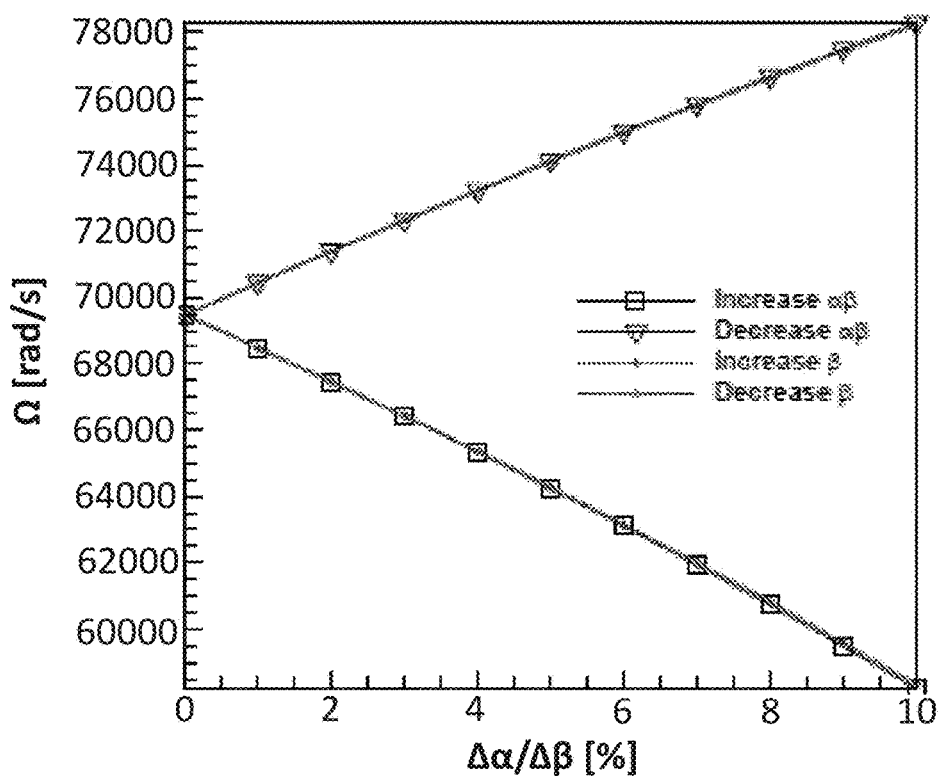
FIGS. 18a and 18b provide data graphs showing the sensitivity of viscoelastic target frequencies $\Omega$ on damping parameters $\alpha$ and $\beta$, where the damping parameters are varied within a 10% margin both simultaneously and individually in accordance with embodiments.
Figure 18B:
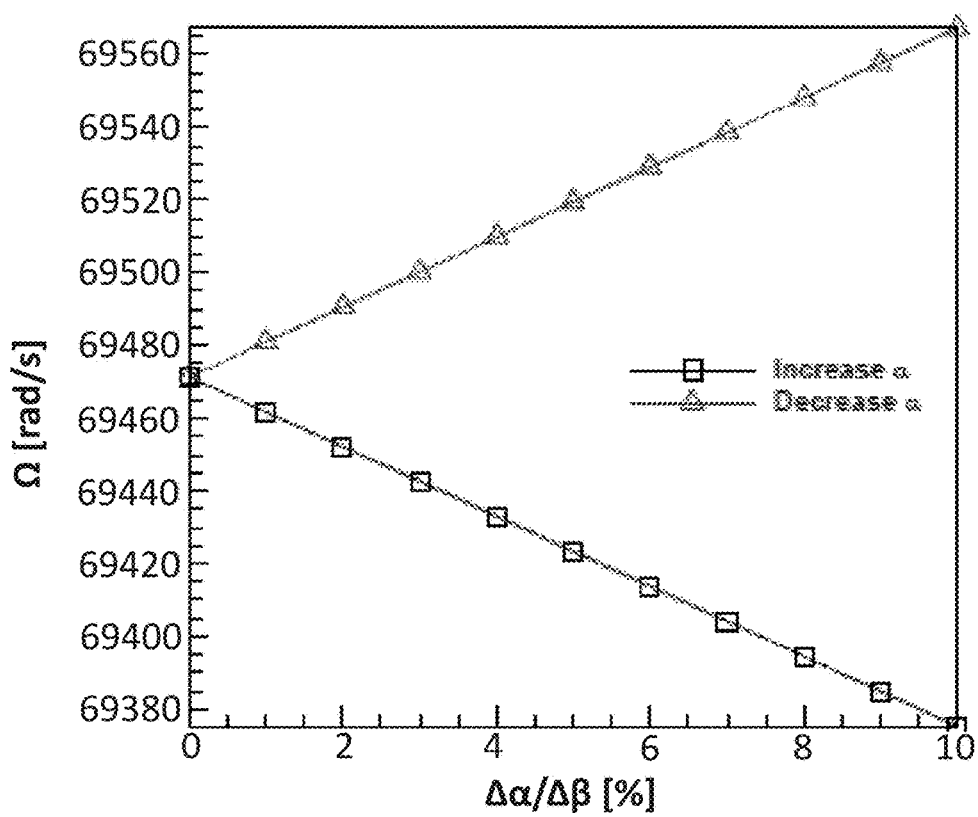

In order to further investigate the sensitivity of eigenfrequency values on viscosity parameters, damping parameters $\alpha$ and $\beta$ are varied within a 10% margin, both simultaneously and individually. Results of the sensitivity analysis are shown in FIGS. 18a and 18b. It is noted that an increase in damping parameters leads to a decrease in viscoelastic target frequencies, whereas a decrease in damping parameters leads to an increase in viscoelastic target frequencies. For an increase of α and β of 10%, the viscoelastic target frequency is decreased by 16:2%. A decrease of α and β of 10% on the other hand leads to an increase in Ω of 12:67%. Furthermore, the damping parameter β has the major influence on the overall change in Ω.

While the material model of the present analysis is calibrated for a specific ECM/cell system (Kim et al., Konno et al., and Schrader et al., all previously cited) elastic eigenfrequencies determined in accordance with embodiments may be expected to decrease with increasing ECM/cell stiffness and to increase with decreasing ECM/cell stiffness regardless of ECM/cell type. Moreover, viscoelasticity is anticipated to lower elastic eigenfrequencies.

Figure 19:
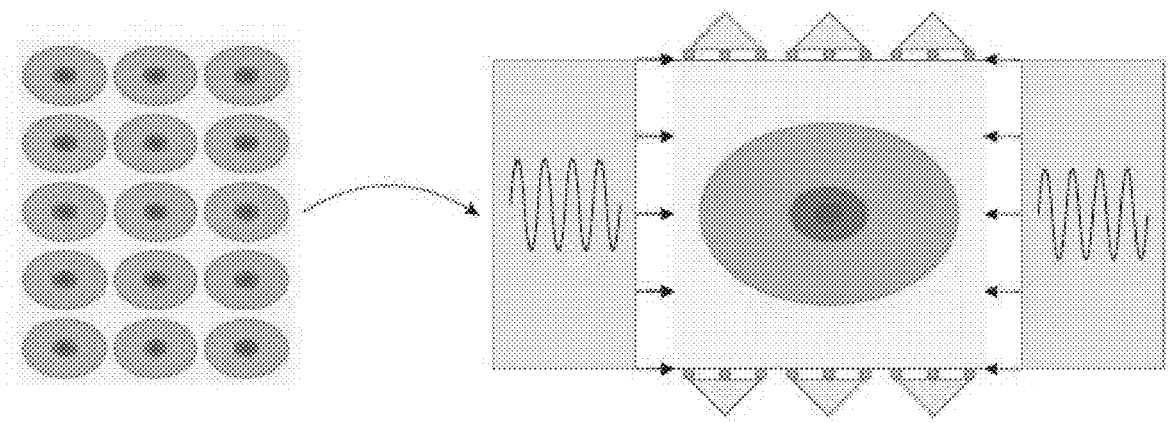
FIG. 19 provides a schematic diagram of the boundary conditions and harmonic excitation used in simulations of the viscoelastic transient cell response at resonance resembling a periodic arrangement of cells within the ECM in accordance with embodiments.

In conclusion, fully nonlinear three-dimensional implicit dynamics simulations of healthy and cancerous cells under resonant harmonic excitation using embodiments of a finite element discretization of the geometrical cell model illustrated in FIG. 16 with a total of 15,215 linear tetrahedral elements are presented. A sketch of the boundary conditions and application of mechanical excitation is shown in FIG. 19. The geometrical model of the cell does not account for the observed increase in nuclear/nucleolar volume. (See, Berman, previously cited). Thus, the simulations represent a conservative estimate of the oncotripsy effect, with nuclear/nucleolar growth expected to further enhance the effect.

With regard to the strength of cellular membranes, several experimental investigations can be found in the literature spanning different measuring techniques. For example, it has been showed that the macroscopic network strength can be traced to the microscopic interaction potential of cytoskeletal components such as actin and cross-linking molecules. In addition, it has been reported that a critical stress level of 30 Pa for a single actin/cross-linking protein bond. (See, e.g., Lieleg, O., et al., 2009. *Biophysical Journal* 96, 4725-4732, the disclosure of which is incorporated herein by reference.) On the macroscopic level, it has been found that the plasma membrane of red blood cells (RBCs) ruptures beyond a critical areal strain of 2-4% under quasistatic conditions, whereby micropipette measurements were employed. (See, e.g., Evans, E. A., et al., 1976. *Biophysical Journal* 16, 585-595, the disclosure of which is incorporated herein by reference.) This investigation was extended to the yield strength of RBC membranes to impulsive stretching by a strong shear flow generated from a laser-induced cavitation bubble, to demonstrate that permanent membrane damage is observed for 50% of the cells above critical areal strains of 40%. (See, e.g., Li, F., et al., 2013. *Biophysical Journal* 105, 872-879, the disclosure of which is incorporated herein by reference.) It has also been reported that the plasma membrane breaks in cells submitted to 20-30% cyclic elongation. (See, e.g., Dreyfuss, D., et al., 2006. Ventilator-Induced Lung Injury, 1st Edition. CRC Press, Boca Raton, Fla., the disclosure of which is incorporated herein by reference.)

Figure 20:
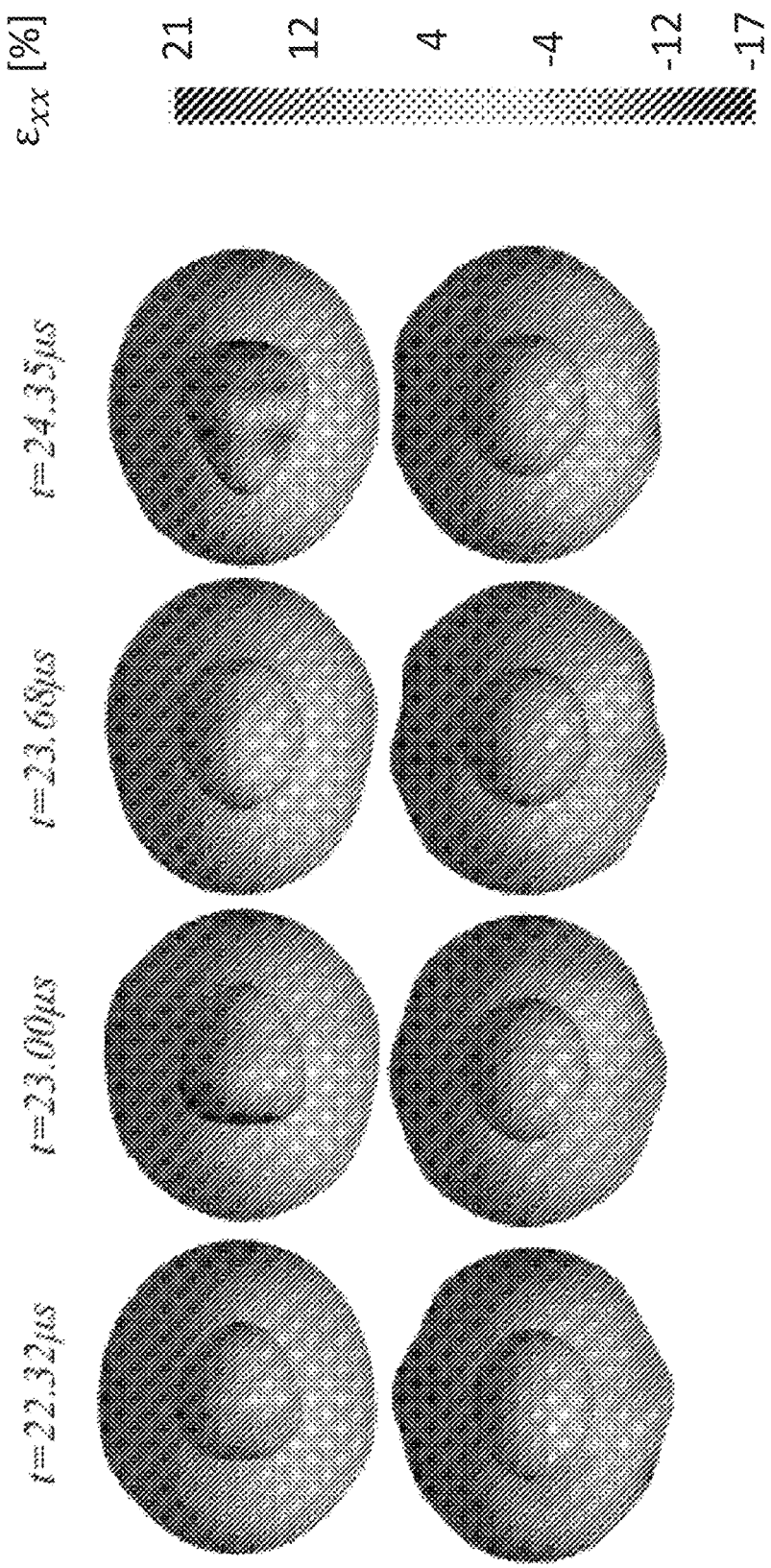
FIG. 20 provides diagrams of the transient response at resonance within the viscoelastic framework in accordance with embodiments, where: (top) is the cancerous cell and (bottom) is the healthy cell.

In the present example, the amplitude of harmonic excitation is set to 0.08 μm and lysis of the cell membranes is expected to occur at a critical strain level of 20% as previously reported. (Dreyfuss et al., previously cited.) In order to test for failure, the true strain in the direction of cyclic excitation in the plasma membrane and nuclear envelope may be tracked. In the elastic case, with viscoelasticity neglected, the rupture strain of the nuclear envelope is reached at time t=20.97 us in cancerous cells, while healthy cells exhibit strain levels below critical values at that time. Consideration of viscoelasticity results in a modest increase the time to lysis, namely t=24.35 μs, with healthy cells still well below critical strain levels at the same time, FIG. 20.

In short, in this example the influence of viscoelasticity on embodiments of methods and systems of performing oncotripsy were studied. Based on eigenfrequencies for both healthy and cancerous cells calculated in the linear elastic framework, eigenfrequencies under viscoelastic conditions have been derived under the assumption of Rayleigh damping. The main effect of viscoelasticity is a modest reduction in the resonant natural frequencies of the cells and an equally modest increase of the time to lysis of the cancerous cells. The simulations predict that embodiments of oncotripsy remains viable when viscoelasticity is taken into account.

Summary

Embodiments have presented systems and methods capable of exploiting spectral gaps between target cancer cells and healthy cells can be exploited to selectively bring such cancerous cells to lysis through the application of carefully tuned ultrasound harmonic excitation, while keeping healthy cells intact. The clinical applicability of such low-intensity ultrasound pulses has been demonstrated in other fields, e.g., as a means of inducing sonoporation and enhanced endocytosis via low frequency ultrasound in the range of 255 kHz. (See, Lentacker, I., et al., 2014. *Advanced Drug Delivery Reviews* 72, 49-64, the disclosure of which is incorporated herein by reference.) In the systems and methods material parameters are presented that may be used to tune harmonic excitation frequencies for lysis of specific cell types. Such material properties include, for example, the hyperplastic behavior of the cytoplasm and nucleoplasm membrane elements of the plasma membrane and nuclear envelope, respectively. Although these terms are described generally herein, it will be noted that specific measurements of the elastic modulus of both cell features, including, for example, the plasma membrane and nuclear envelope are readily available in the literature. (See, e.g., Dahl, K. N., et al., 2004. *Journal of Cell Science* 117, 4779-4786, the disclosure of which is incorporated herein by reference.) Moreover, different experimental techniques may be used, as will be known in the art, to determine relevant material parameters for different cell types allowing for creation of other cell model as needed. Therefore, although embodiments described herein may discuss specific cell types (e.g., hepatocellular carcinoma cells described by Kim et al., previously cited), it will be understood that equivalent studies have been conducted on numerous potential diseased cell types and may be used in accordance with the systems and methods described herein. Moreover, as discussed other nucleolar material parameters not measured in experiments may be inferred using scaling parameters, such as those suggested by Konno et al., previously cited.

Finally, although the present model has been described in relation to total cell lysis, the systems and methods are amenable to a number of extensions. One such extension is to take viscoelastic properties into account and model the effect of time-varying material properties on the transient response of a cell at resonance. Indeed, several investigations suggest a viscoelastic behavior of both the cell nucleus (Guilak, F., *Biochemical and Biophysical Research Communications* 269, 781-786, the disclosure of which is incorporated herein by reference) and plasma membrane (Evans, E. A. & Hochmuth, R. M., 1976. *Biophys J.* 16 (1), 1-11; and Jay, A. W. L., 1973. *Biophys J.* 13 (11), 1166-1182, the disclosures of which are incorporated herein by reference). Exemplary extensions may include strain-softening material models could reveal valuable insights into the failure mechanisms induced by resonance. Of special interest and promise are models that explicitly account for the intricate cytoskeletal network composed of microtubules, intermediate filaments and interconnected microfilaments, however, many other additional models may be included in such analyses.

Doctrine of Equivalents

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

What is claimed is:

1. A method of performing oncotripsy comprising:
    identifying a target cell type in an organism and identifying at least one healthy cell type present in the organism near the target cell type;
    modeling the target cell type and the at least one healthy cell type to identify a plurality of eigenfrequencies for the target cell type and a plurality of eigenfrequencies for the at least one healthy cell type, wherein the plurality of eigenfrequencies for the target cell type and the plurality of eigenfrequencies for the at least one healthy cell type are determined by modeling a plasma membrane, a nuclear envelope, cytoplasm, nucleoplasm, and a nucleolus for the target cell type and the at least one healthy cell type, wherein the plasma membrane is modeled as a lipid bilayer composed of two regular layers of lipid molecules, and wherein the nuclear envelope is modeled as a double lipid bilayer membrane;
    selecting a target cell eigenfrequency from the plurality of eigenfrequencies for the target cell type such that a spectral gap exists between the target cell eigenfrequency and all eigenfrequencies in the plurality of eigenfrequencies associated with the at least one healthy cell type;
    subjecting at least one area of the organism containing target cells to an ultrasonic harmonic excitation tuned to the target cell eigenfrequency for a duration sufficient to induce a transient destructive resonance within the target cell type,
    wherein the spectral gap is sufficiently large such that the transient destructive resonance is induced within the target cell type and not induced within the at least one healthy cell type.

2. The method of claim 1, wherein the transient destructive resonance disrupts nuclear membranes of the target cells and induces lysis.

3. The method of claim 1, wherein a growth rate of the target cell resonant mode is greater than a growth rate of the healthy cell resonant mode.

4. The method of claim 1, wherein the ultrasonic harmonic excitation has a frequency range of about 80 kHz, a duration of at least 70 microseconds, and a power density of at least 0.8 W/cm$^2$.

5. The method of claim 1, wherein the plasma membrane, the nuclear envelope, the cytoplasm, the nucleoplasm, and the nucleolus are each modeled as a spheroidal shape.

6. The method of claim 5, wherein the plurality of eigenfrequencies for the target cell type and the plurality of eigenfrequencies for the at least one healthy cell type are determined by considering a nucleus-to-cell volume ratio of the target cell type and the at least one healthy cell type.

7. The method of claim 5, wherein a nucleus-to-cell volume ratio of greater than one is indicative of a target cell.

8. The method of claim 1, wherein the plurality of eigenfrequencies of the target cell type and the plurality of eigenfrequencies for the at least one healthy cell type are determined by modelling elasticity of the plasma membrane, the nuclear envelope, the cytoplasm, the nucleoplasm, and the nucleolus using a Mooney-Rivlin-type strain energy density calculation.

9. The method of claim 1, wherein the plurality of eigenfrequencies for the target cell type and the plurality of eigenfrequencies for the at least one healthy cell type are determined using a finite element mesh.

10. The method of claim 9, wherein the target cells and the at least one healthy cell type are approximated as elliptical cells embedded into an extra-cellular matrix modelled using a standard Bloch wave theory.

11. The method of claim 1, wherein the cytoplasm, the nucleoplasm and the nucleolus for the target cell type and the at least one healthy cell type are discretized using linear tetrahedral elements, and wherein the plasma membrane and the nuclear envelope are discretized using linear triangular membrane elements.

12. The method of claim 1, wherein the target cell is a cancerous cell.

13. The method of claim 12, wherein the target cell eigenfrequency is around 500,000 rad/s.

14. The method of claim 1, wherein the target cell eigenfrequency for the target cell type is selected such that the ultrasonic harmonic excitation induces lysis in a specific cell component of the target cell type.

15. The method of claim 14, wherein the target cell type is cancerous, and the transient destructive resonance is induced within the plasma membrane of the target cell.

16. A method of determining oncotripsy conditions comprising:
    identifying a target cell type in an organism and identifying at least one healthy cell type present in the organism near the target cell type;
    modeling the target cell type and the at least one healthy cell type to determine a target cell ultrasonic eigenfrequency for the target cell type,
        wherein the modeling comprises identifying a plurality of ultrasonic eigenfrequencies for the target cell type and a plurality of eigenfrequencies for the at least one healthy cell type,
        wherein the plurality of ultrasonic eigenfrequencies for the target cell type and the plurality of eigenfrequencies for the at least one healthy cell type are determined by modeling a plasma membrane, a nuclear envelope, cytoplasm, nucleoplasm, and a nucleolus for the target cell type and the at least one healthy cell type,
        wherein the plasma membrane is modeled as a lipid bilayer composed of two regular layers of lipid molecules,
        wherein the nuclear envelope is modeled as a double lipid bilayer membrane,
        wherein a spectral gap exists between the target cell ultrasonic eigenfrequency and all of the plurality of eigenfrequencies for the at least one healthy cell type, and
        wherein the spectral gap is sufficiently large such that the transient destructive resonance is induced within the target cells prior to a transient destructive resonance being induced within a healthy cell resonant mode of the at least one healthy cell type.

17. The method of claim 16, wherein the plasma membrane, the nuclear envelope, the cytoplasm, the nucleoplasm, and the nucleolus are each modeled as a spheroidal shape.

18. The method of claim 17, wherein the plurality of ultrasonic eigenfrequencies of the target cell type and the plurality of ultrasonic eigenfrequencies of the at least one healthy cell type are determined by considering one or more of the following properties: a nucleus-to-cell volume ratio of the target cell type and the at least one healthy cell type, the stiffness of an extra-cellular matrix associated with the target cell type and the at least one healthy cell type, and the softness of a cellular material of the target cell type and the at least one healthy cell type.

19. The method of claim 18, wherein the nucleus-to-cell volume ratio of the target cell type is greater than a nucleus-to-cell volume ratio of the at least one healthy cell type.

20. The method of claim 18, wherein the extra-cellular matrix of the target cell type is stiffer than that of the at least one healthy cell type.

21. The method of claim 18, wherein the cellular material of the target cell type is softer than that of the at least one healthy cell type.

22. The method of claim 16, wherein the plurality of ultrasonic eigenfrequencies of the target cell type and the plurality of ultrasonic eigenfrequencies for the at least one healthy cell type are determined by modelling elasticity of the plasma membrane, the nuclear envelope, the cytoplasm, the nucleoplasm, and the nucleolus using a Mooney-Rivlin-type strain energy density calculation.

23. The method of claim 16, wherein the plurality of ultrasonic eigenfrequencies of the target cell type and the plurality of ultrasonic eigenfrequencies for the at least one healthy cell type are determined using a finite element mesh.

24. The method of claim 23, wherein the target cell type and the at least one healthy cell type are approximated as elliptical cells embedded into an extra-cellular matrix modelled using a standard Bloch wave theory.

25. The method of claim 16, wherein the cytoplasm, the nucleoplasm, and the nucleolus of the target cell type and the at least one healthy cell type are discretized using linear tetrahedral elements, and wherein the plasma membrane and the nuclear envelope are discretized using linear triangular membrane elements.

26. A system for performing oncotripsy comprising:
a source of ultrasonic harmonic excitation; and
a source controller for selecting an ultrasonic harmonic excitation frequency from a plurality of eigenfrequencies corresponding to a target cell type such that a spectral gap exists between the selected ultrasonic harmonic excitation frequency and all eigenfrequencies from a plurality of eigenfrequencies associated with at least one healthy cell type,
wherein the spectral gap is sufficiently large such that a transient destructive resonance is induced within the target cell type and not induced within the at least one healthy cell type,
wherein the plurality of eigenfrequencies corresponding to the target cell type and the plurality of eigenfrequencies associated with the at least one healthy cell type are determined by modeling a plasma membrane, a nuclear envelope, cytoplasm, nucleoplasm, and a nucleolus for the target cell type and the at least one healthy cell type,
wherein the plasma membrane is modeled as a lipid bilayer composed of two regular layers of lipid molecules, and
wherein the nuclear envelope is modeled as a double lipid bilayer membrane.

* * * * *